US00RE46558E

(19) United States
(12) Reissued Patent
Sherris et al.

(10) Patent Number: US RE46,558 E
(45) Date of Reissued Patent: Sep. 26, 2017

(54) COMPOSITIONS AND METHODS TO TREAT DISEASES CHARACTERIZED BY CELLULAR PROLIFERATION AND ANGIOGENESIS

(71) Applicant: Paloma Pharmaceuticals, Inc., Charlottesville, VA (US)

(72) Inventors: David I. Sherris, Jamaica Plain, MA (US); Manjinder Gill, SAS Nagar (IN); Fupeng Ma, Melrose, MA (US); Sanjivanjit Kaur Bhal, Oakville (CA); Robert Dunn-Dufault, Guelph (CA); Miklos Feher, New York, NY (US); Peter Redden, Oakville (CA); Jonathan Schmidt, Elora (CA)

(73) Assignee: PALOMA PHARMACEUTICALS, INC., Charlottesville, VA (US)

(21) Appl. No.: 14/789,935

(22) Filed: Jul. 1, 2015

Related U.S. Patent Documents

Reissue of:
(64) Patent No.: 8,475,776
Issued: Jul. 2, 2013
Appl. No.: 11/680,292
Filed: Feb. 28, 2007

U.S. Applications:
(63) Continuation-in-part of application No. 11/412,618, filed on Apr. 27, 2006, now abandoned.

(60) Provisional application No. 60/777,318, filed on Feb. 28, 2008, provisional application No. 60/675,707, filed on Apr. 28, 2005.

(51) Int. Cl.

| | |
|---|---|
| ***A61K 8/00*** | (2006.01) |
| ***A61K 39/00*** | (2006.01) |
| ***A61K 31/517*** | (2006.01) |
| ***A01N 43/14*** | (2006.01) |
| ***A61K 31/44*** | (2006.01) |
| ***C07D 311/80*** | (2006.01) |
| ***A61K 31/4433*** | (2006.01) |
| ***A61K 31/366*** | (2006.01) |
| ***A61K 31/382*** | (2006.01) |
| ***A61K 31/473*** | (2006.01) |
| ***A61K 45/06*** | (2006.01) |
| ***A61K 31/352*** | (2006.01) |
| ***A61K 31/353*** | (2006.01) |
| ***C07D 311/18*** | (2006.01) |
| ***C07D 405/06*** | (2006.01) |
| ***A61K 31/192*** | (2006.01) |
| ***A61K 31/235*** | (2006.01) |
| ***C07D 405/12*** | (2006.01) |
| ***A61K 47/48*** | (2006.01) |
| ***C07C 65/40*** | (2006.01) |
| ***C07C 69/78*** | (2006.01) |
| ***C07D 311/16*** | (2006.01) |
| ***C07D 239/90*** | (2006.01) |

(52) U.S. Cl.
CPC ..... *C07D 311/80* (2013.01); *A61K 31/192* (2013.01); *A61K 31/235* (2013.01); *A61K 31/352* (2013.01); *A61K 31/353* (2013.01); *A61K 31/366* (2013.01); *A61K 31/382* (2013.01); *A61K 31/4433* (2013.01); *A61K 31/473* (2013.01); *A61K 31/517* (2013.01); *A61K 45/06* (2013.01); *A61K 47/48246* (2013.01); *A61K 47/48384* (2013.01); *C07C 65/40* (2013.01); *C07C 69/78* (2013.01); *C07D 239/90* (2013.01); *C07D 311/16* (2013.01); *C07D 311/18* (2013.01); *C07D 405/06* (2013.01); *C07D 405/12* (2013.01)

(58) Field of Classification Search
CPC ..... A61K 31/352
See application file for complete search history.

(56) References Cited

U.S. PATENT DOCUMENTS

| | | | | |
|---|---|---|---|---|
| 4,248,861 | A | 2/1981 | Schutt | |
| 4,299,826 | A | 11/1981 | Luedders | |
| 4,363,812 | A | 12/1982 | Kuriyama et al. | |
| 5,853,742 | A | 12/1998 | Bartolone et al. | |
| 6,399,082 | B1 | 6/2002 | Ganemo | |
| 6,632,835 | B2 * | 10/2003 | Schmidt et al. | C07D 407/04 514/452 |
| 6,849,757 | B2 | 2/2005 | Kawai et al. | |
| 6,908,917 | B2 | 6/2005 | Ortwine | |
| 7,169,942 | B2 | 1/2007 | Moore et al. | |
| 7,326,447 | B2 | 2/2008 | Taugerbeck et al. | |
| 7,378,421 | B2 | 5/2008 | Mujica-Fernaud et al. | |
| 9,381,187 | B2 | 7/2016 | Sherris | |
| 2002/0115711 | A1 | 8/2002 | Schmidt | |
| 2002/0119914 | A1 | 8/2002 | Zhu et al. | |

(Continued)

FOREIGN PATENT DOCUMENTS

| | | |
|---|---|---|
| EP | 0 645 382 A1 | 3/1995 |
| IN | 200400392 | 2/2006 |

(Continued)

OTHER PUBLICATIONS

JM Schmidt et al. Synthesis and Evaluation of a Novel Nonsteroidal-Specific Endothelial Cell Proliferation Inhibitor. J. Med. Chem. 2003, 46, 1289-1292.*

Q Xue et al. Palomid 529, a Novel Small-Molecule Drug, Is a TORC1/TORC/2 Inhibitor That Reduces Tumor Growth, Tumor Angiogenesis, and Vascular Permeability.Cancer Res 2008; 68(22):9551-7.*

Requirement for Restriction/Election dated Jun. 4, 2014, in U.S. Appl. No. 13/901,011, 10 pages.

Applicant-Initiated Interview Summary dated Oct. 10, 2014, in U.S. Appl. No. 13/901,011, 3 pages.

(Continued)

*Primary Examiner* — Bruce Campell
(74) *Attorney, Agent, or Firm* — Hoxie & Associates LLC

(57) ABSTRACT

Described herein are compositions and methods for preventing and/or treating diseases involving aberrant angiogenesis employing one or more benzo[c]chromen-6-one derivatives.

29 Claims, 6 Drawing Sheets

(56) References Cited

U.S. PATENT DOCUMENTS

| | | | |
|---|---|---|---|
| 2004/0162281 | A1 | 8/2004 | Babu et al. |
| 2004/0198750 | A1 | 10/2004 | Green et al. |
| 2004/0242593 | A1 | 12/2004 | Moore, II et al. |
| 2005/0245490 | A1 | 11/2005 | Pinney et al. |
| 2006/0257337 | A1 | 11/2006 | Sherris |
| 2007/0197567 | A1 | 8/2007 | Sherris |
| 2014/0105920 | A1 | 4/2014 | Sherris |

FOREIGN PATENT DOCUMENTS

| | | | |
|---|---|---|---|
| WO | WO 93/1529 | | 8/1993 |
| WO | WO 93/15219 | A1 | 8/1993 |
| WO | WO 00/56303 | A2 | 9/2000 |
| WO | WO 01/46110 | A2 | 6/2001 |
| WO | WO 02/094984 | | 11/2002 |
| WO | WO 02/094984 | A2 | 11/2002 |
| WO | WO 03/105842 | A1 | 12/2003 |
| WO | WO 2004/073612 | | 9/2004 |
| WO | WO 2004/073612 | A2 | 9/2004 |
| WO | WO 2007/101247 | A2 | 9/2007 |
| WO | WO 2010/129622 | A1 | 11/2010 |

OTHER PUBLICATIONS

Response to Requirement for Restriction/Election filed Dec. 4, 2014, in U.S. Appl. No. 13/901,011, 9 pages.

Non-Final Office Action dated Jan. 12, 2015, in U.S. Appl. No. 13/901,011, 12 pages.

Reply to Office Action filed Jul. 13, 2015, in U.S. Appl. No. 13/901,011, 12 pages.

Final Office Action dated Aug. 21, 2015, in U.S. Appl. No. 13/901,011, 11 pages.

Notice of Appeal filed Feb. 22, 2016, in U.S. Appl. No. 13/901,011, 2 pages.

Submission Under 37 C.F.R. § 1.114 filed Sep. 22, 2016, U.S. Appl. No. 13/901,011, 12 pages.

Notice of Allowance and Fee(s) Due mailed Oct. 25, 2016, in U.S. Appl. No. 13/901,011, 20 pages.

Adams, R. et al., "Structure of Cannabinol. I. Preparation of an Isomer, 3-hydroxy-1-amyl-6,6,9-trimethy1-6-dibenzopyran," Journal of the American Chemical Society, 1940, 62, 2197-2200, XP002563538, Chemical Abstracts only.

Aoyama, N. et al., "Coumarin Derivatives for Quantitative Determination of Peroxidation-Active Substances by Chemiluminescence Analysis," 1993, XP002563539, Chemical Abstracts only.

Carl, P. et al., "Protease-Activated 'Prodrugs' for Cancer Chemotherapy," Proceedings of the National Academy of Sciences, 1980, 77 (4), 2224-2228.

Children's Hospital, Atopic Dermatitis—Treatment, Care, & FAQ, retrieved Jul. 6, 2012, from http://childrenshospital.org/az/Site609/mainpageS609P4.html, 8 pages.

Dement Abstract for IN 200400392, retrieved Jul. 9, 2007, 3 pages, document indicates IN 200400932 published Feb. 24, 2006.

Devlin, J. et al., "Synthesis and Structure-Activity Relationships of 5H,11H[2]Benzopyrano [4,3-g] [1]benzopyran-9-carboxylic Acids," Journal of Medicinal Chemistry, 1977, 20 (2), 205-209.

Farina, V. et al., "The Stille Reaction," Organic Reactions, 1997, 50, XP002563537, Chemical Abstracts only.

Garazd, Y. et al., "Modified Coumarins. 6. Synthesis of Substituted 5,6,-Benzopsoralens," Chemistry of Natural Compounds, 2002, 38 (5), 424-433, XP002563541, Chemical Abstracts only.

International Preliminary Report on Patentability for related International Application No. PCT/US2007/062971, dated Sep. 2, 2008.

Kenner, G. et al., "Oxidative Cyclization of 2-Biphenylcarboxylic Acid," Tetrahedron, 1957, 1, 259-268, XP002563536, Chemical Abstracts only.

Kurita, M. et al., "Induction of Keratinocyte Apoptosis by Photosensitizing Chemicals Plus UVA," Journal of Dermatological Science, 2007, 45 (2), 105-112.

Larrosa, M. et al., "Urolithins, Ellagic Acid-Derived Metabolites Produced by Human Colonic Microflora, Exhibit Estrogenic and Antiestrogenic Activities," Journal of Agricultural and Food Chemistry, 2006, 54, 1611-1620.

Liu, S. et al., "Facilitation of Retinal Function Recovery by Coumarin Derivatives," Journal of Ocular Pharmacology and Therapeutics, 1997, 13 (1), 69-79.

Lopez-Gonzalez, J. et al., "Apoptosis and Cell Cycle Disturbances Induced by Coumarin and 7-Hydroxycouramin on Human Lung Carcinoma Cell Lines," Lung Cancer, 2004, 43 (3), 275-283.

Rigaudy, J. et al., "Dehydration of Meso-dihydroanthracene Alcohols. 9,10-Dihydro-9-anthryl Tertiary Carbinols. A Case of Elimination (of water) According to Hofmann's Rule," Comptes Rendus, 1957, 245, 86-88, XP002563540, Chemical Abstracts only.

Sapuntsova, S. et al., "Proliferative Processes in the Epidermis of Patients with Atopic Dermatitis Treated with Thymodepressin," Bulletin of Experimental Biology and Medicine, 2002, 133 (5), 488-490.

The Acne Resource Center Online, Your Online Guide to Skin Care, retrieved Jul. 6, 2012, from http ://www.acne -resource.org/understanding-acne/understanding-index.html, 2 pages.

Umamoto, H. et al., "Fluorescent Whitening Agents for Synthetic Fibers. 18. Annenation Effects in the Fluorescence of Some Coumarins," Kogyo Kagaku Zasshi, 1971, 74 (10), 2123-2126, XP002563541, Chemical Abstracts only.

Vilar, S. et al., "Design, Synthesis, and Vasorelaxant and Platelet Antiaggregatory Activities of Coumarin-Resveratrol Hybrids," Bioorganic & Medicinal Chemistry Letters, 2006, 16, 257-261.

Wolff, M., Ed., Burger's Medicinal Chemistry and Drug Discovery, Fifth Edition, vol. 1: Priciples and Practice, 1995, 975-977.

Xie, T. et al., "Regulation of Keratinocyte Proliferation in Rats with Deep, Partial-Thickness Scald: Modulation of Cyan D1-Cyclin-Dependent Kinase 4 and Histone H1 Kinase Activity of M-Phase Promoting Factor," Journal of Surgical Research, 2008, 147 (1), 9-14.

Yano, K. et al., "Targeted Overexpression of the Angiogenesis Inhibitor Thrombosponclin-1 in the Epidermis of Transgenic Mice Prevents Ultraviolet-B-Induced Angiogenesis and Cutaneous Photo-Damage," The Journal of Investigative Dermatology, 2002, 118 (5), 800-805.

Yoo, H. et al., "Biodegradable Nanoparticles Containing Doxorubicin-PLGA Conjugate for Sustained Release," Pharmaceutical Research, 1999, 16 (7), 1114-1118.

Zhang, Y. et al., "Study on the Synthesis and Spectra Characteristics of Coumarins," Ranliao Yu Ranse Bianjibu, 2003, 40 (2), 68-70, XP002563541, Chemical Abstracts only.

Carl et al. Proc. Natl. Acad. Sci. 77(4);224-2228 (1980).*

Manfred E. Wolff, Burger's Medicinal Chemistry and Drug Discovery, 5th edition, vol. 1, 1995, pp. 975-997.*

International Search Report and Written Opinion of the International Searching Authority for related International Application No. PCT/US2006/040242, dated Dec. 9, 2008.

Written Opinion of the International Searching Authority for related International Application No. PCT/US2007/062971, dated Aug. 30, 2007.

Kenner et al., Document No. XP-002563536, 1957.

Farina et al., Document No. XP-002563537, 1997.

Adams et al., Document No. XP-002563538, 1940.

Document No. XP-002563539, 1993.

Rigaudy et al., Document No. XP-002563540, 1957.

Zhang et al., Document No. XP-002563541, 2003.

* cited by examiner

COMPOSITIONS AND METHODS TO TREAT DISEASES CHARACTERIZED BY CELLULAR PROLIFERATION AND ANGIOGENESIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This patent application is *a reissue application of U.S. Pat. No. 8,475,776, issued on Jul. 2, 2013, from U.S. patent application Ser. No. 11/680,292, filed Feb. 28, 2007, which is* a continuation-in-part of U.S. patent application Ser. No. [11,412,618] *11/412,618*, filed Apr. 27, 2006, which in turn claims priority to and the benefit of U.S. Provisional Application Ser. No. 60/675,707, filed Apr. 28, 2005, and also claims priority to and benefit of U.S. Provisional Application Ser. No. 60/777,318, filed Feb. 28, 2006, all of which applications are incorporated by reference herein in their entirety.

FIELD OF THE INVENTION

The present invention relates to compositions and methods for preventing and/or treating diseases associated with cellular proliferation and/or angiogenesis. The current invention is directed in part to a series of chemical compositions that demonstrate therapeutic benefit in diseases involving abnormal cellular proliferation, abnormal angiogenesis or a combination thereof.

BACKGROUND OF THE INVENTION

Blood vessels that make up the cardiovascular system may be broadly divided into arteries, veins and capillaries. Arteries carry blood away from the heart at relatively high pressure; veins carry blood back to the heart at low pressure, while capillaries provide the link between the arterial and venous blood supply During embryonic development, vessels are first formed through vasculogenesis, utilizing pluripotent endothelial cell precursors. Later, through arteriogenesis, larger blood vessels are formed possessing a more complex structure of endothelial cells, smooth muscle cells and pericytes (tunica media). Although arteriogenesis is not considered to occur in the adult, blood vessels may be formed in the adult through vasculogenesis and notably a process known as angiogenesis. Under normal conditions, angiogenic neovascularization occurs during such conditions as wound repair, ischemic restoration and the female reproductive cycle (generating endometrium forming the corpus luteum and during pregnancy to create the placenta). The capillaries, relatively simple vessels formed by angiogenesis, lack a developed tunica as they arc predominantly composed of endothelial cells and to a lesser extent perivascular cells and basement membrane.

Cancer is a disease state characterized by the uncontrolled proliferation of altered tissue cells. Tumors less than a few millimeters in size utilize nearby normal vessels to provide nutrients and oxygen. However, above this critical size, cancer cells utilize angiogenesis to create additional vascular support. Normally, angiogenesis is kept in check by the body naturally creating angiogenic inhibitors to counteract angiogenic factors. However, the cancer cell changes this balance by producing angiogenic growth factors in excess of the angiogenic inhibitors, thus favoring blood vessel growth. Cancer initiated angiogenesis is not unlike angiogenesis observed during normal vessel growth. Angiogenic factors pass from the tumor cell to the normal endothelium, binding the endothelial cell, activating it and inducing endothelial signaling events leading to endothelial cell proliferation. Endothelial tubes begin to form, homing in toward the tumor with the formation of capillary loops. Capillaries then undergo a maturation process to stabilize loop structure.

There have been several chemotherapeutic approaches targeted against tumor cell proliferation including alkylating agents, antimitotics, antimetabolites and antibiotics. These act preferentially on the rapidly proliferating tumor cells. Hormonal therapy with anti-estrogens or anti-androgens is another approach to attacking cancer cells that work by inhibiting the proliferative action of the required hormone. Although anti-cancer agents fall into specific classifications, it is not uncommon for agents to act by multiple modes of action. For example, the anti-estrogen tamoxifen has been shown to have anti-proliferative activity on cancer cells and endothelial cells (anti-angiogenic) by an estrogen independent mechanism. Taxol, an antimitotic agent acting on microtubules has also demonstrated anti-angiogenic properties, possibly by inducing apoptosis of endothelial cells through Bcl-2 phosphorylation.

Cancer is but one disease associated with a pathological neovasculature. A wide variety of diseases involving aberrant angiogenesis exist in nature. These diseases utilize the same steps involved in normal capillary growth but do so in aberrant manner creating capillaries which lack a high degree of stability and function. Agents capable of inhibiting angiogenesis would be expected to exert activity on a variety of pathological neovascular diseases.

Angiogenesis may be considered a key component in the pathogenesis of a number of diseases. If through therapeutic intervention angiogenesis could be slowed down or eliminated, anti-angiogenic agents would then be expected to abolish or lessen a variety of neovasculature associated diseases. Anti-angiogenic therapy will likely be very effective at suppressing tumor growth by denying the tumors a blood supply. However, anti-angiogenic therapy may prove more effective in combination with other therapies aimed directly at the tumor cells. Chemical agents that demonstrate both anti-angiogenic and tumor directed properties would be advantageous in this regard.

Thus, there remains a need to develop agents that demonstrate anti-proliferative effects against human endothelial cells for the treatment of a variety of diseases, including, but not limited to, cancer, in addition to an inhibitory effect directly on cancer cells for the treatment of tumors, or other cells acting as an initiator of angiogenesis for diseases outside of cancer. And at least in some cases, the ability to have a sustained half-life through the creation of analogs with modifications that inhibit metabolism and hence clearance or loss of activity, and show little or no toxicity. The present invention seeks to meet these and other needs.

BRIEF SUMMARY OF THE INVENTION

The present invention relates to compositions and methods for treating diseases associated with cellular proliferation and/or angiogenesis. The current invention is directed in part to a series of chemical compositions that demonstrate a therapeutic benefit in diseases involving abnormal cellular proliferation, abnormal angiogenesis or a combination thereof.

One embodiment of the present invention is directed to compositions used to prevent and/or treat abnormal cellular proliferation. In one aspect, the invention is directed to a series of benzo[c]chromen-6-one derivatives that demonstrate enhanced anti-proliferative effects against human endothelial cells for the treatment of a variety of diseases, including, but not limited to, cancer. These agents have a dual anti-angiogenic, tumor cell anti-proliferative activity.

In another aspect of the present embodiment, the invention is directed to a series of benzo[c]chromen-6-one derivatives that demonstrate enhanced anti-proliferative effects against human endothelial cells for the treatment of a variety of diseases including, but not limited to, cancer with minimal or no anti-proliferative effects directly on tumor cells. In other words, these agents show predominantly anti-angiogenic activity.

Another embodiment of the present invention is directed to a series of benzo[c]chromen-6-one derivatives that demonstrate enhanced anti-proliferative effects against human endothelial cells for the treatment of a variety of diseases including, but not limited to, cancer. In one aspect, the enhanced anti-proliferative effect against human endothelial cells is complimented by an anti-proliferative inhibitory effect directly on tumor cells for the treatment of cancer. In another aspect, the enhanced anti-proliferative effect against endothelial cells is complimented with an anti-proliferative inhibitory effect on pathologically relevant cells specific to the disease, outside of cancer, for example keratinocytes for skin diseases.

In yet another embodiment, the present invention is directed toward methods of administering a therapeutically effective amount of one or more compositions described herein to a subject in need thereof. In one aspect, the targeted subject has been diagnosed with or is predisposed toward one or more diseases associated with abnormal cellular proliferation and/or angiogenesis, including for example, a cancer.

Other features and advantages of the invention will be apparent from the following detailed description of embodiments thereof.

DETAILED DESCRIPTION OF THE INVENTION

Figure 1:
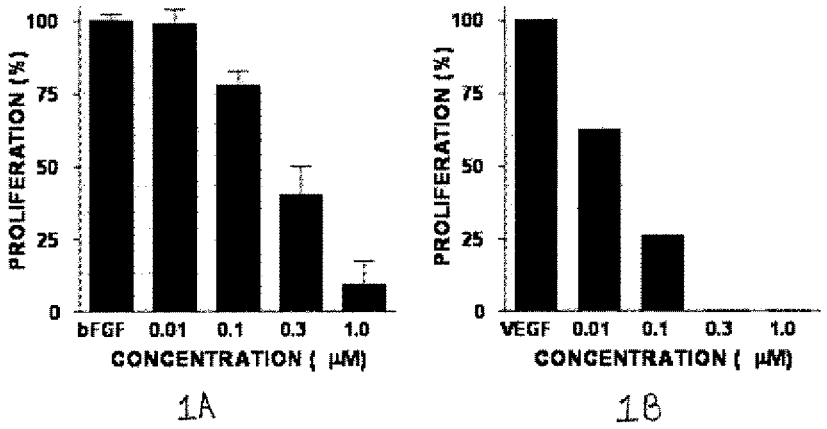
FIG. 1A is a bar graph showing inhibition of bFGF-stimulated endothelial cell proliferation by Palomid 529.
FIG. 1B is a bar graph showing inhibition of VEGF-stimulated endothelial cell proliferation by Palomid 529.

The present invention relates to compositions and methods for preventing and/or treating diseases associated with unwanted cellular proliferation and/or angiogenesis. The current invention is directed in part to a series of chemical compositions that demonstrate therapeutic benefit in diseases involving abnormal cellular proliferation, abnormal angiogenesis or a combination thereof. In a particular aspect, the instant invention relates to benzo[c]chromen-6-one derivatives that demonstrate their effect on diseases characterized by abnormal proliferation, abnormal angiogenesis or a combination thereof.

The term "derivative" is understood by those skilled in the art. For example, a derivative can be understood as a chemical compound that is produced from another compound of similar structure in one or more steps, such as illustrated in Table I (infra) for benzo[c]chromen-6-one.

Disease therapeutic agents currently under development are based on a variety of targeting strategies. One strategy is the use of natural inhibitors of angiogenesis such as thrombospondin, angiostatin and endostatin. Another strategy is the use of agents that block receptors required to stimulate angiogenesis, such as antagonists of the VEGF receptor. A third strategy is the inhibition of enzymes which allow new blood vessels to invade surrounding tissues, for example, inhibitors of matrix metalloproteinases. Another strategy for inhibiting angiogenesis is through the use of integrin antagonists such as $\alpha v\beta 1$ antibodies or small molecule drugs through the inhibition of endothelial cell adhesion effecting capillary tube formation.

Angiogenesis is an attractive therapeutic target for cancer treatment due to its selectivity of action. Blood vessels in growing tumors are in a microenvironment conducive to cellular activation and rapid proliferation whereas blood vessels in most normal tissues are quiescent. This microenvironment inducing cellular activation and rapid proliferation are believed to be the physiological differences that allow the selective targeting of blood vessels in the tumor by anti-angiogenic agents.

The present invention relates to a therapeutic formulation comprising one or more compositions useful in the treatment of unwanted cellular proliferation and/or angiogenesis and/or keratinocyte proliferation. The present invention also relates to a therapeutic formulation comprising one or more compositions useful in the treatment of cancer as well as other diseases characterized by the undesired excessive, abnormal stimulation or proliferation of, for example endothelial cells or other cells resulting in such diseases including, but not limited to, ocular diseases of corneal, retinal or anterior chamber neovasculature, cancer (including, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, hemangioma, medullary carcinoma, bronchogenic carcinoma, renal cell carcinoma, hepatoma, bile duct carcinoma, choriocarcinomas, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, osteosarcoma, meningioma, melanoma, neuroblastoma, retinoblastoma, acousticneuroma, neurofibromas, trachoma and pyogenic granulomas, acute lymphocytic leukemia and acute myelocytic leukemia, chronic leukemia, polycythemia vera, lymphoma, multiple myeloma, Waldenstrom's macroblobulinemia, and heavy chain disease), hereditary hemorrhagic telangiectasia, solid or blood born tumors, acquired immune deficiency syndrome, post-menopausal symptoms, osteoporosis, cardiovascular disease, Alzheimer's disease, to reduce the incidence of strokes, as an alternative to prior estrogen replacement therapies, vascular malformations, abnormal wound healing, inflammatory and immune disorders, gout, and other ocular diseases (retinal/choroidal, corneal, neoplastic and anterior chamber neovascular, including but not limited to macular degeneration, diabetic retinopathy, retinopathy of prematurity, corneal graft rejection, multifocal choroiditis, Best's disease, Stargardt's disease, cb1C type of cobalamin deficiency, hyperviscosity syndrome, Sorsby's fundus dystrophy, pseudoxanthoma elasticum, rubeosis iridis, Osler Weber syndrome (Osler-Weber-Rendu disease), keratoconjunctivitis, Vitamin A deficiency, phylectenulosis, contact lens over wear, infection (including but not limited to bacterial, viral, parasitic, or fungal), atopic and superior limbic dermatitis, chronic uveitis, chronic vitritis, Eales' disease, radial keratotomy, uncharacteristic proliferation of fibrovascular or fibrous tissue including all forms of proliferative vitreoretinopathy whether or not associated with diabetes, chronic retinal detachment, trauma (including but not limited to abrasion, previous surgery with complications such as corneal allograft rejection, alkaline burns, acid burns or hydrocarbon burns, mechanical or thermal damage to Bruch's membrane), pterygium, neoplasia (including but not limited to retinoblastoma and melanoma)), arthritis (rheumatoid and osteoarthritis) and skin diseases (psoriasis, atopic dermatitis, photodamage). Other diseases associated with angiogenesis include Sjögren's syndrome, systemic lupus, polyarteritis, pemphigoid, sickle cell anemia, Paget's disease, vein or artery occlusion, carotid obstructive disease, Lyme disease, Behcet's disease, bartonelosis, arteriosclerosis, induction of amenorrhea to block ovulation or to prevent implantation by the blastula, surgical adhesions and chronic inflammation (including but not limited to ulcerative colitis and Crohn's disease).

In accordance with the present invention, there is provided pharmaceutical compositions comprising Formula I:

(I)

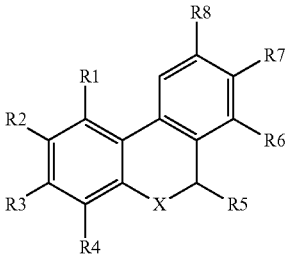

where,

R1=H or alkyl;

R2=H, OH, O-alkyl, amino, O-heterocyc, O-aryl, O-substituted alkyl, where substitution is e.g. halo, aryl, or heteroaryl, O—Ac, O—PO3, O—SO3, or OSO2NH2;

R3-H, OH, O-alkyl, O—CH2Aryl, O—CH2heteroaryl, O-alkylaryl O-acyl, or nitro;

R4=H, Alkyl, CH2Aryl, substituted alkyl, OH, O-alkyl, O-aryl, OCH2Aryl, OCH2Heteroaryl, O-Acyl, OPO3, OSO3, or OSO2NH2;

R5=H, Oxo, aryl, hydroxyl, alkyl, or O-alkyl;

R6=H;

R7=H, Acyl, substituted alkyl, where substitution is e.g. hydroxyl or sulfamoyl, alkyl, O-alkyl, or O-substituted alkyl where substitution is O—PO3 or OSO3;

R8=H; and

X=O, N, or S.

In accordance with the present invention, there is provided pharmaceutical compositions comprising Formula II:

(II)

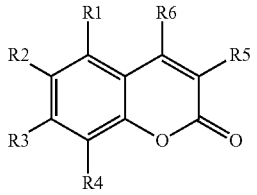

where,

R1=H or alkyl;

R2=H, O-alkyl, OH, amino, O-heterocyc, O-aryl, O-substituted alkyl where substitution is e.g. halo, aryl, or heteroaryl, O—Ac, O—PO3, O—SO3, or OSO2NH2;

R3=H, O-alkyl, O-substituted alkyl where substitution is aryl or heteroaryl, OH, O-acyl, or nitro;

R4=H, Alkyl, CH2Aryl, substituted alkyl, O), O-alkyl, O-aryl, OCH2Aryl, OCH2Heteroaryl, O-Acyl, OPO3, OSO3, or OSO2NH2;

R5=H, Aryl, heteroaryl or substituted alkyl; and

R6=H, Alkyl, or Aryl.

In accordance with the present invention, there is provided pharmaceutical compositions comprising Formula III:

(III)

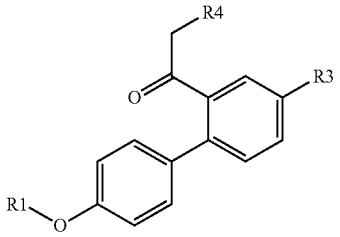

where,

R1=alkyl or N;

R2=alkyl or H;

R3=Acetyl; and

R4=H or Alkyl.

In accordance with the present invention, there is provided pharmaceutical compositions comprising Formula IV:

(IV)

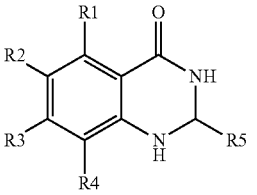

where,

R1=H or F;

R2=H or nitro;

R3=H;

R4=H; and

R5=alkyl, substituted alkyl or aryl.

In accordance with the present invention, there is provided a pharmaceutical composition comprising a therapeutically effective amount of one or more benzo[c]chromen-6-one derivatives having the following structure depicted in Table I:

TABLE I

| Structural formula of benzo[c]chromen-6-one derivatives |
|---|
| 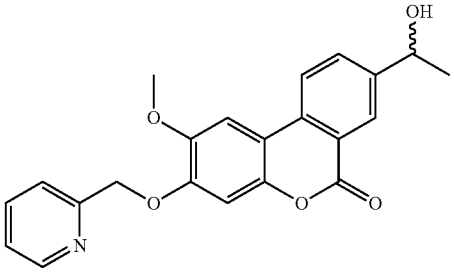 SG00526 |
| 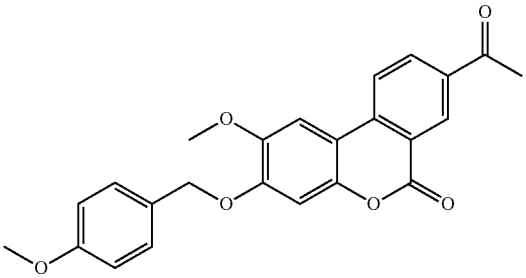 SG00527 |
| 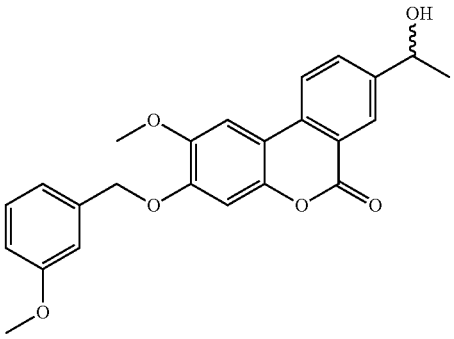 SG00528 |
| 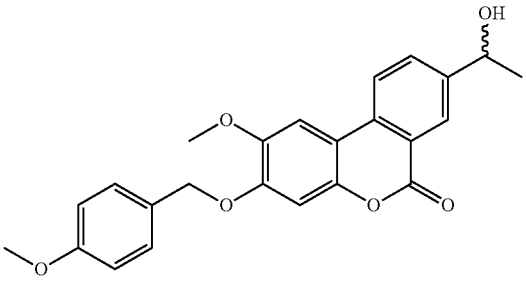 SG00529 |

TABLE I-continued

| Structural formula of benzo[c]chromen-6-one derivatives |
|---|
| 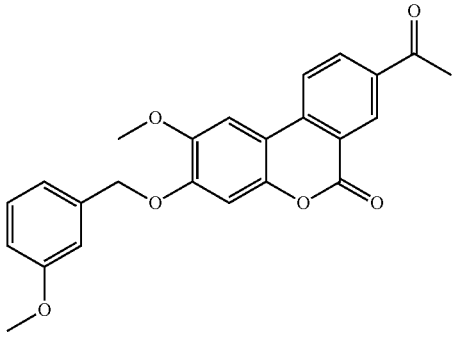 SG00530 |
| 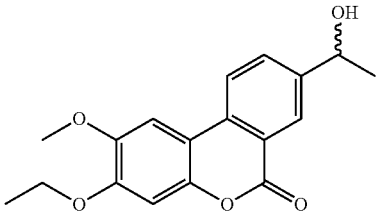 SG00531 |
| 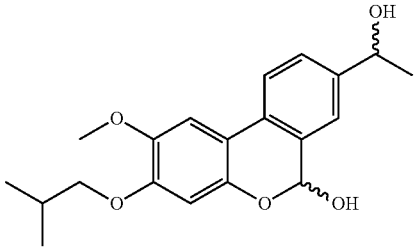 SG00532 |
| 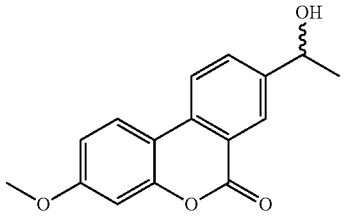 SG00533 |
| 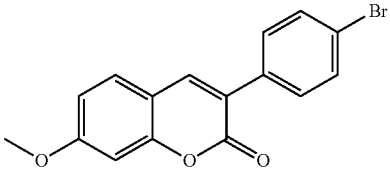 SG00535 |
| 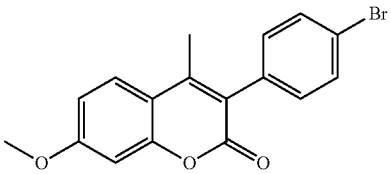 SG00536 |

TABLE I-continued
Structural formula of benzo[c]chromen-6-one derivatives
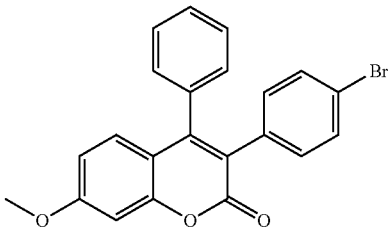
SG00537
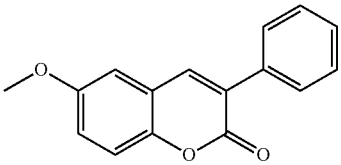
SG00538
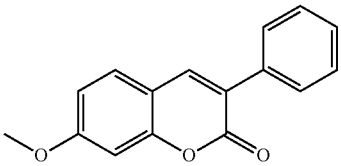
SG00539
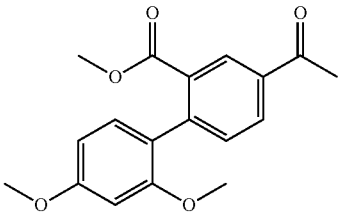
SG00540
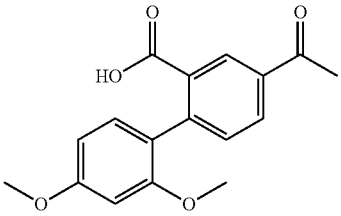
SG00272
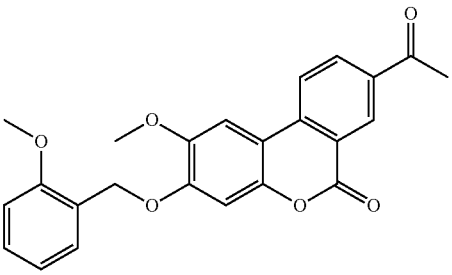
SG00541
TABLE I-continued
Structural formula of benzo[c]chromen-6-one derivatives
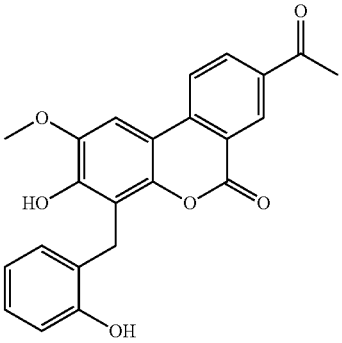
SG00542
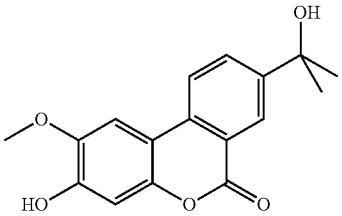
SG00543
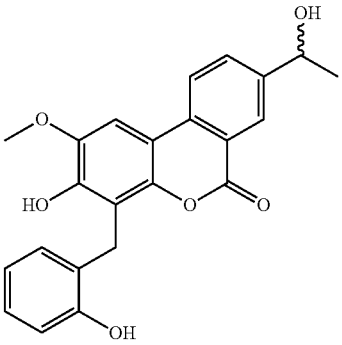
SG00544
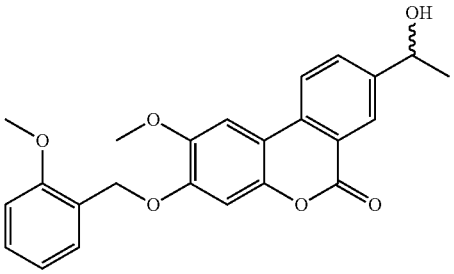
SG00545

TABLE I-continued
Structural formula of benzo[c]chromen-6-one derivatives
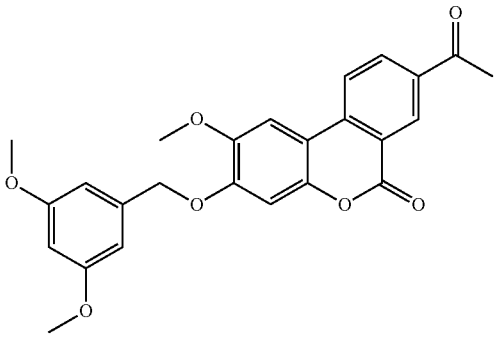
SG00546
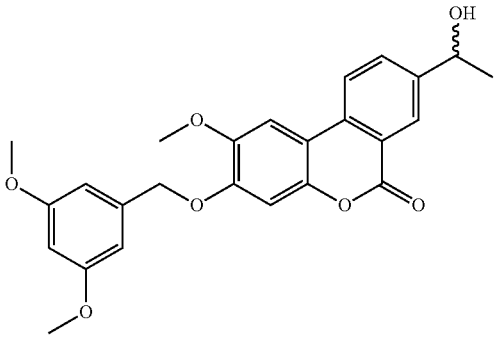
SG00547
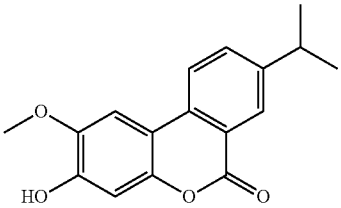
SG00548
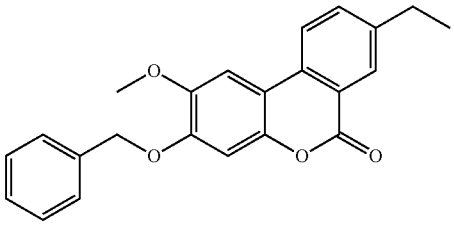
SG00549
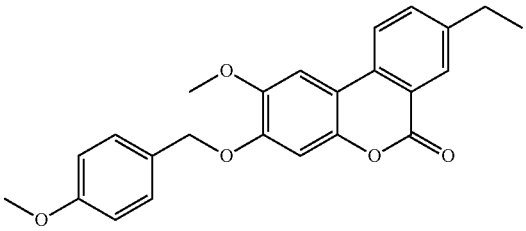
SG00550
TABLE I-continued
Structural formula of benzo[c]chromen-6-one derivatives
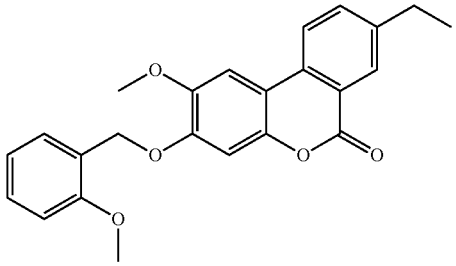
SG00551
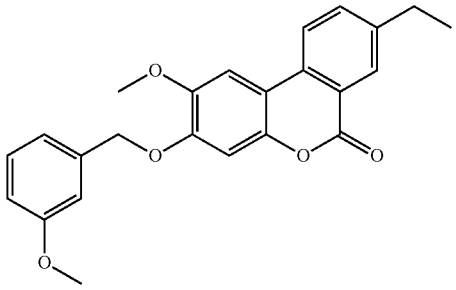
SG00552
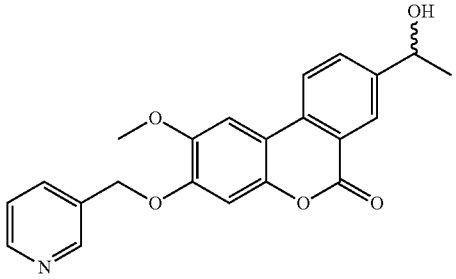
SG00553
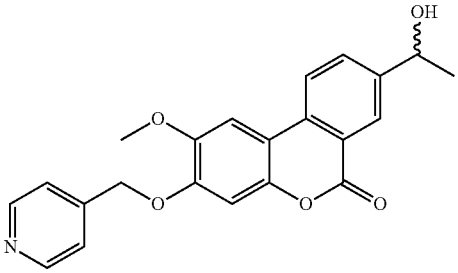
SG00554
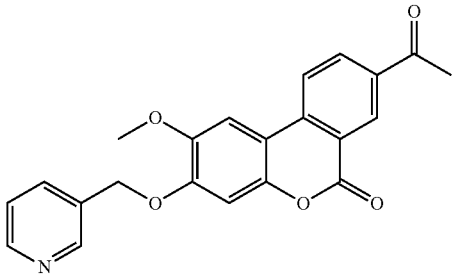
SG00555

TABLE I-continued
Structural formula of benzo[c]chromen-6-one derivatives
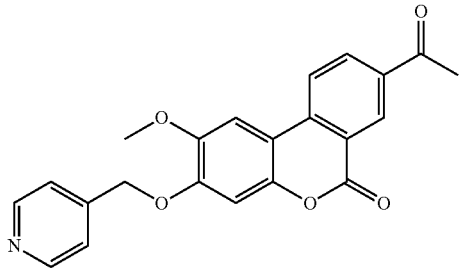
SG00556
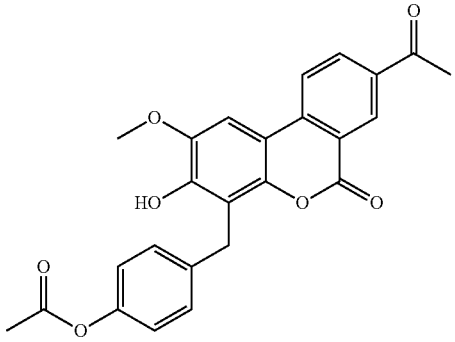
SG00557
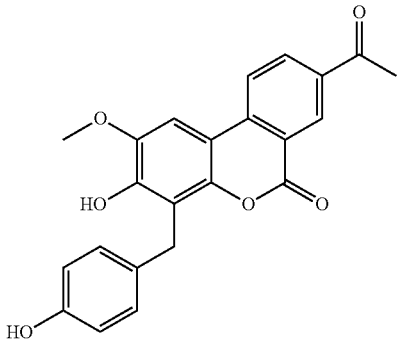
SG00558
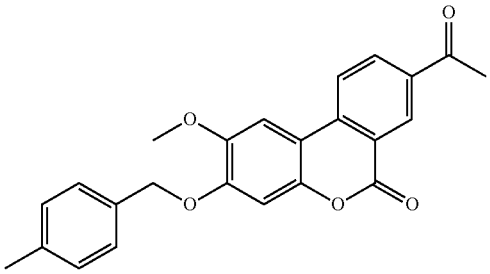
SG00559
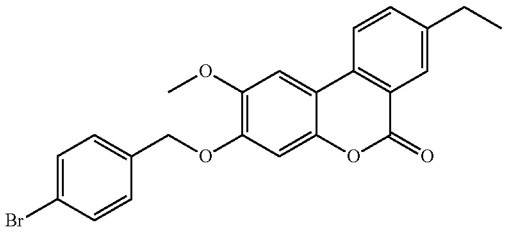
SG00560
TABLE I-continued
Structural formula of benzo[c]chromen-6-one derivatives
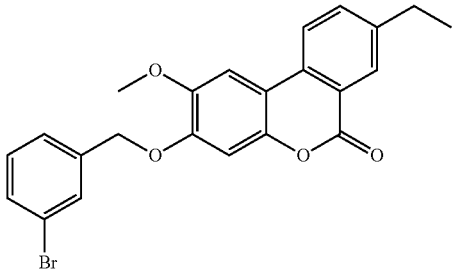
SG00561
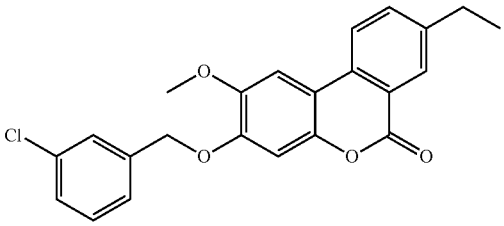
SG00562
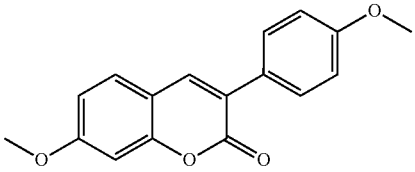
SG00563
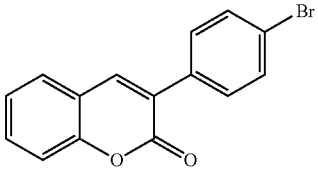
SG00564
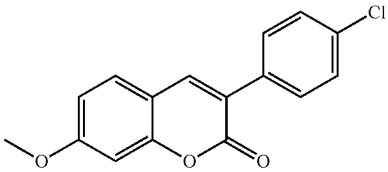
SG00565
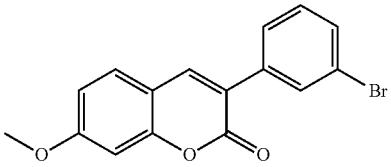
SG00566
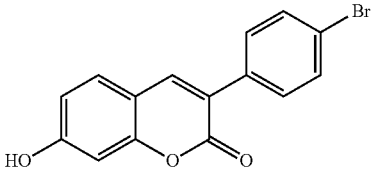
SG00567

TABLE I-continued
Structural formula of benzo[c]chromen-6-one derivatives
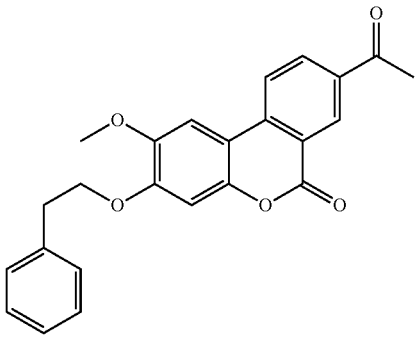
SG00568
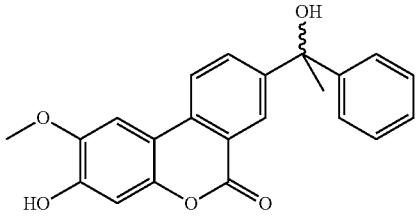
SG00569
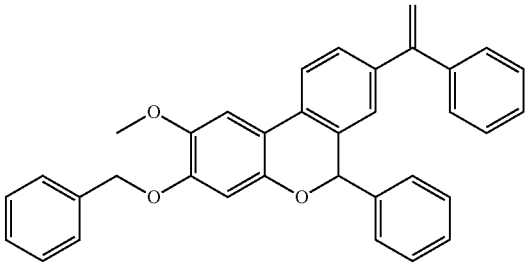
SG00570
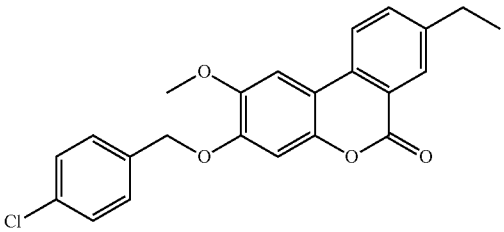
SG00571
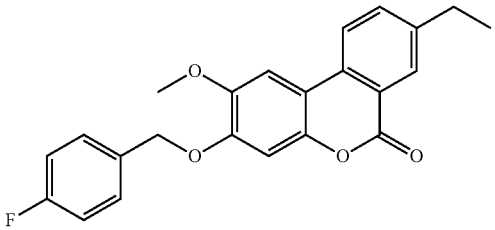
SG00572
TABLE I-continued
Structural formula of benzo[c]chromen-6-one derivatives
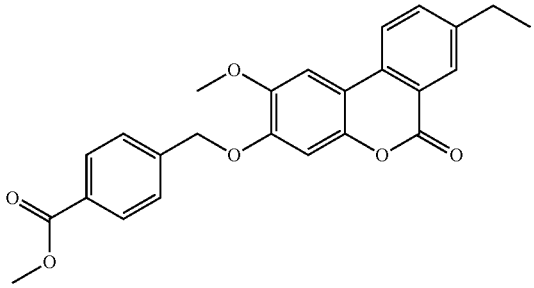
SG00573
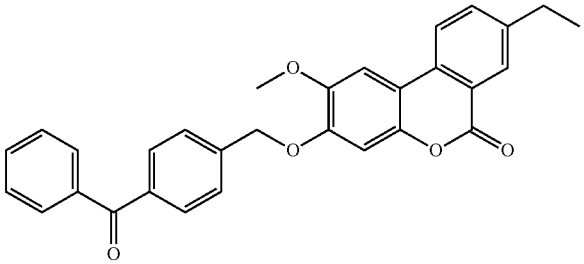
SG00574
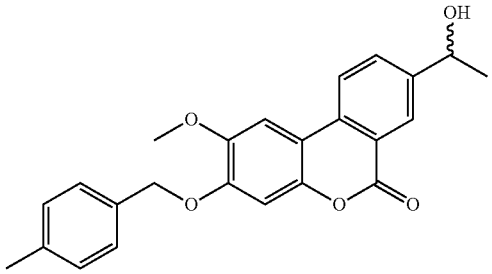
SG00575
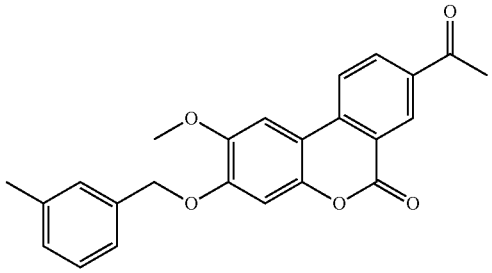
SG00576
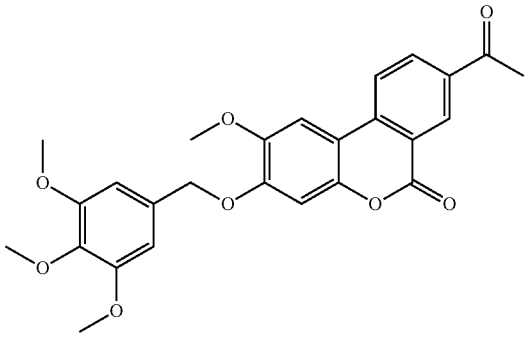
SG00577

TABLE I-continued
Structural formula of benzo[c]chromen-6-one derivatives
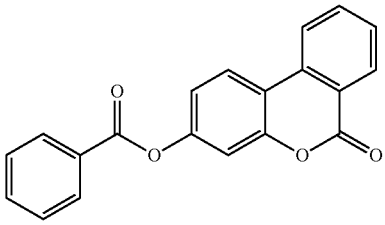
SG00579
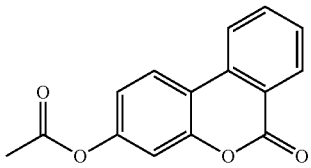
SG00580
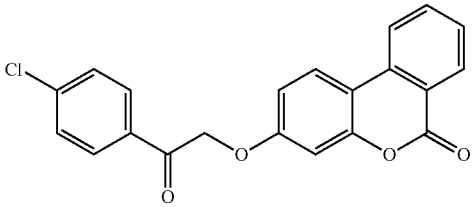
SG00581
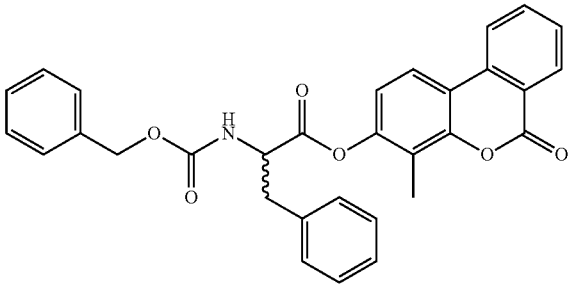
SG00582
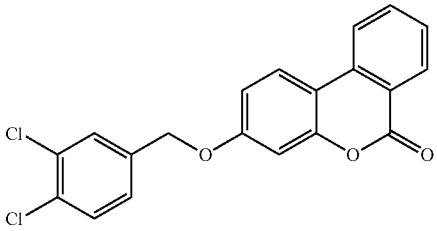
SG00583
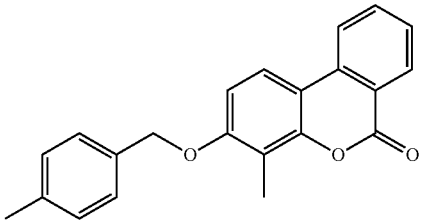
SG00584
TABLE I-continued
Structural formula of benzo[c]chromen-6-one derivatives
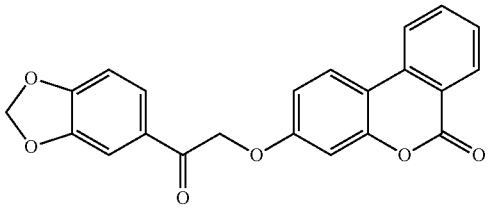
SG00585
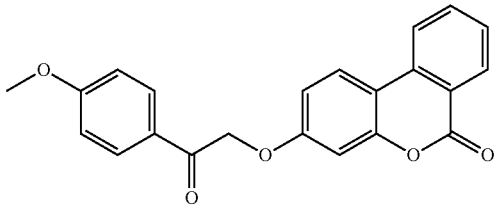
SG00586
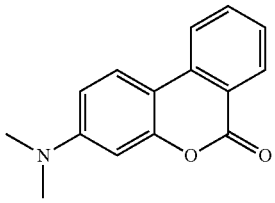
SG00587
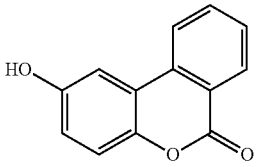
SG00588
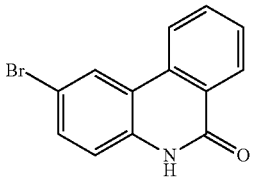
SG00589
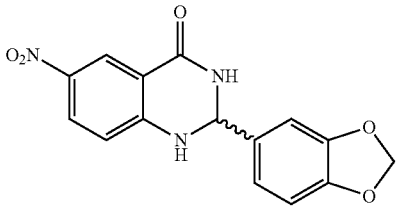
SG00590

TABLE I-continued
Structural formula of benzo[c]chromen-6-one derivatives
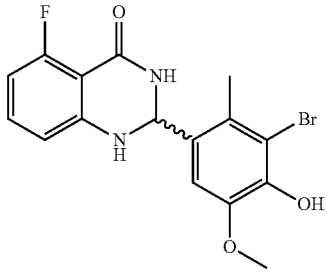
SG00591
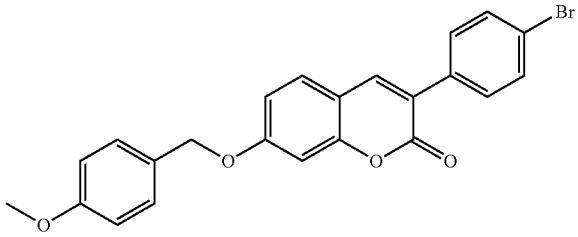
SG00592
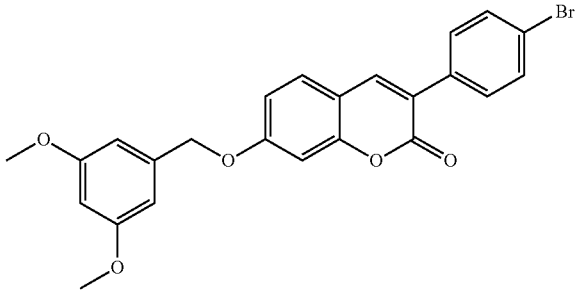
SG00593
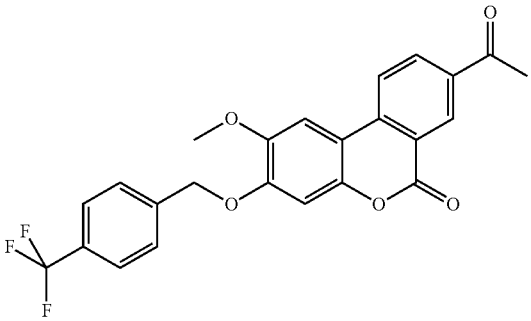
SG00594
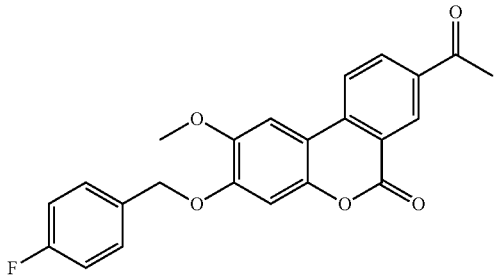
SG00595
TABLE I-continued
Structural formula of benzo[c]chromen-6-one derivatives
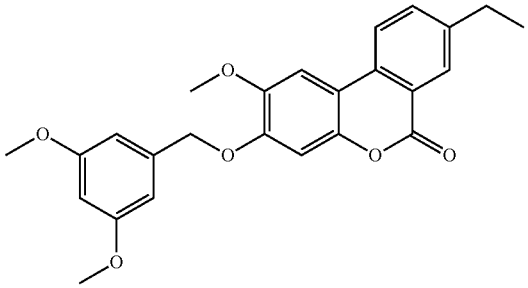
SG00596
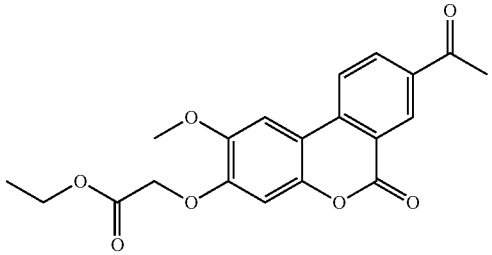
SG00597
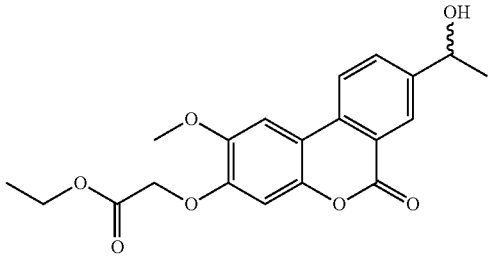
SG00598
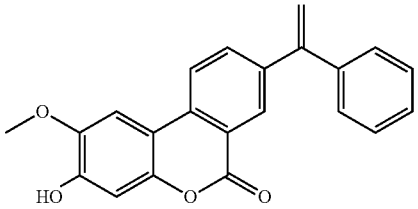
SG00599
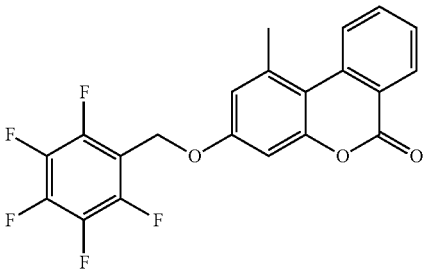
SG00600

TABLE I-continued
Structural formula of benzo[c]chromen-6-one derivatives
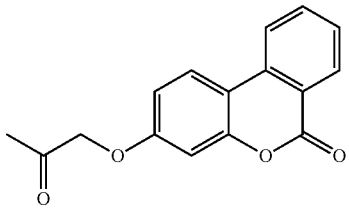
SG00601
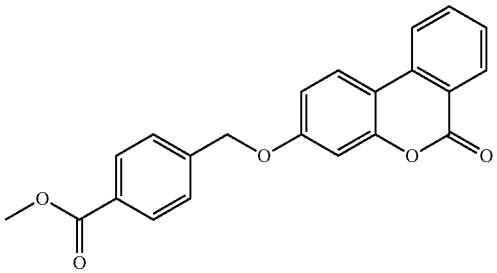
SG00602
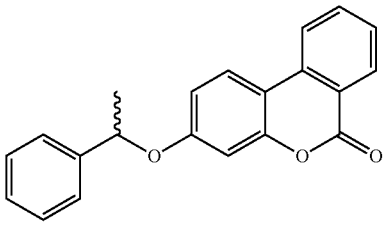
SG00603
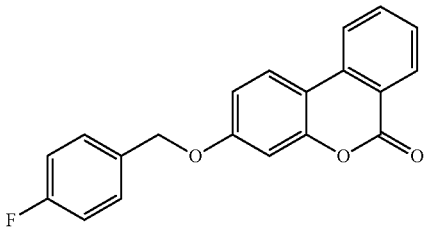
SG00604
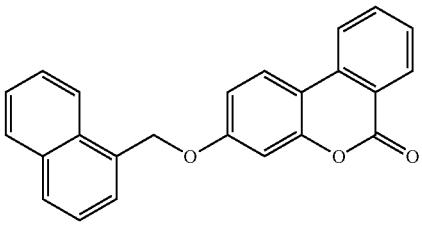
SG00605
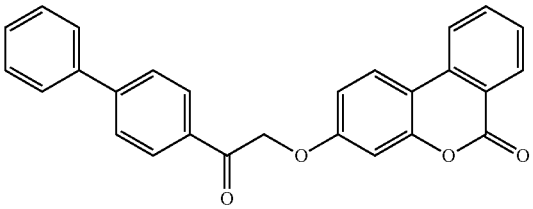
SG00606
TABLE I-continued
Structural formula of benzo[c]chromen-6-one derivatives
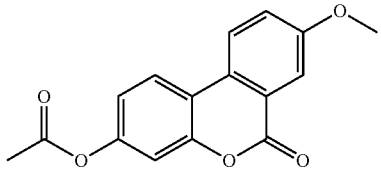
SG00607
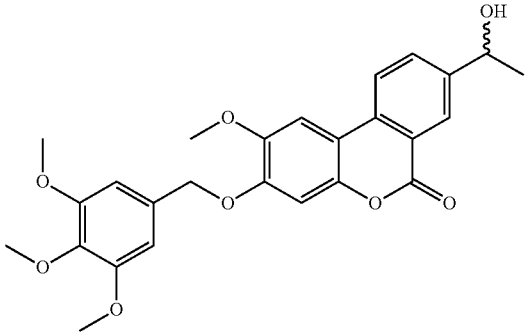
SG00609
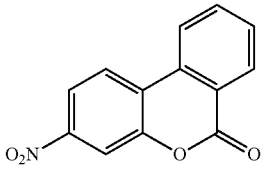
SG00610
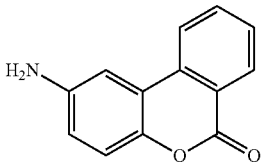
SG00611
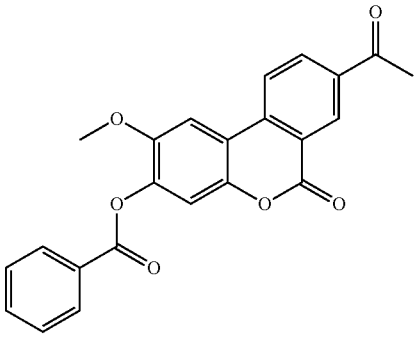
SG00612

TABLE I-continued
Structural formula of benzo[c]chromen-6-one derivatives
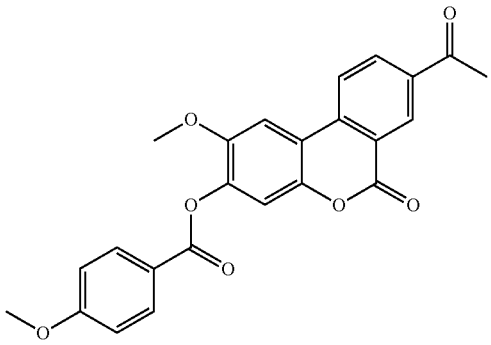
SG00613
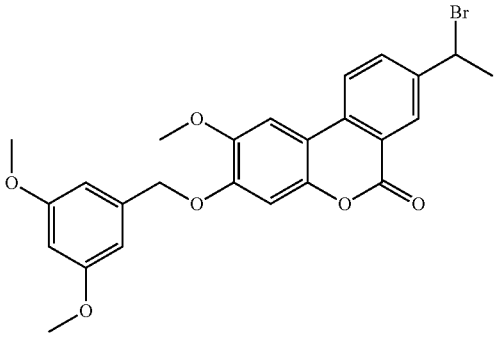
SG00614
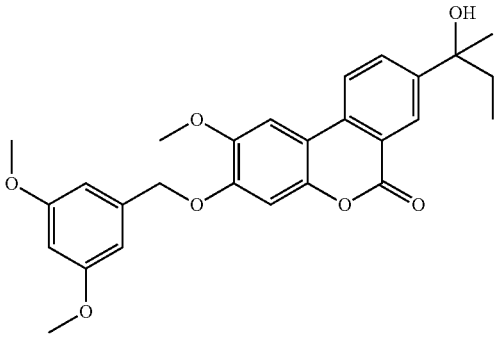
SG00615
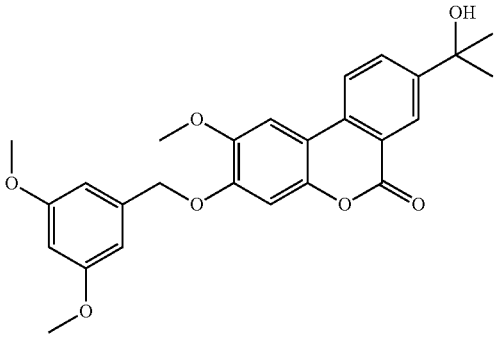
SG00616
TABLE I-continued
Structural formula of benzo[c]chromen-6-one derivatives
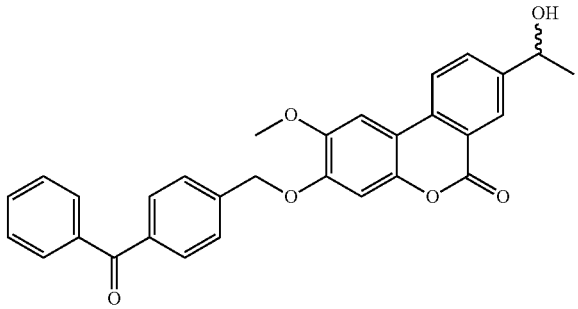
SG00617
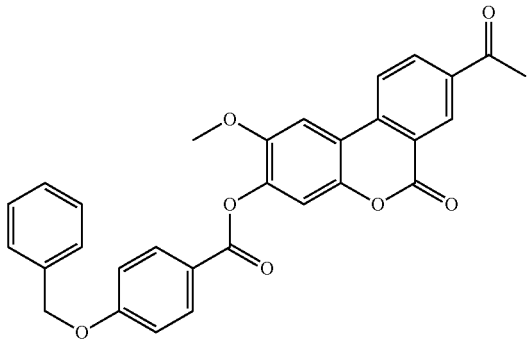
SG00618
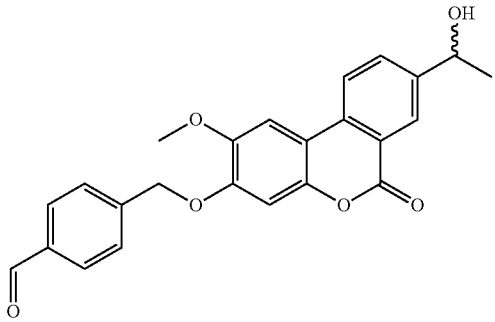
SG00619
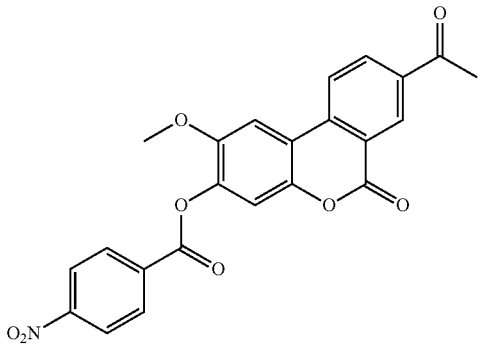
SG00620

TABLE I-continued

| Structural formula of benzo[c]chromen-6-one derivatives |
|---|
| 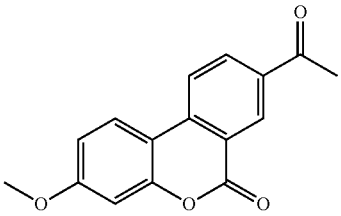 SG00273 |
| 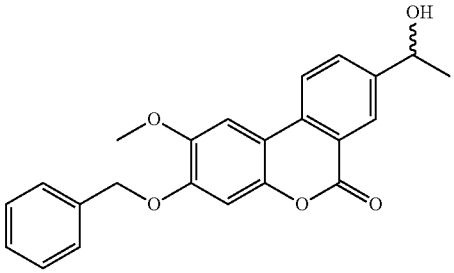 SG00393 |
| 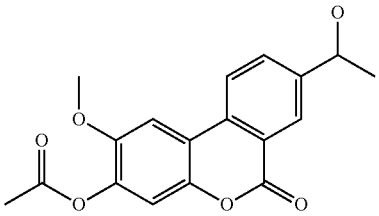 SG00477 |
| 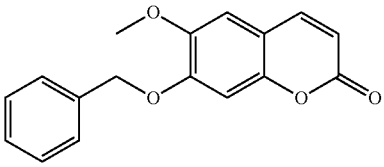 SG00519 |
| 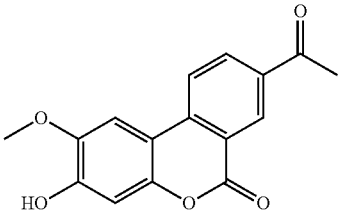 SG00292 |
| 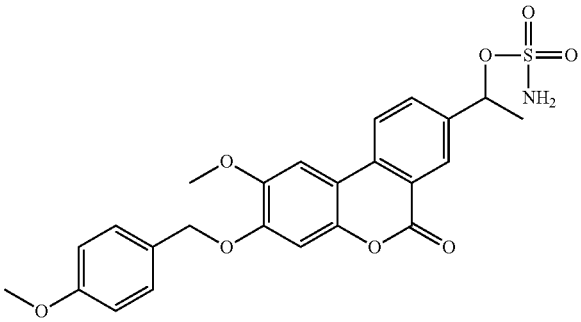 SG00629 |

The individual benzo[c]-chromen-6-one derivatives of Table I are identified by the designation "SG" followed by a number. They are alternatively referred to herein by the designation "Palomid" followed by the same number, i.e. the terms "SG" and "Palomid" are used interchangeably throughout this application.

The compounds of Table I exhibit anti-angiogenic and/or anti-keratinocyte activities. Those skilled in the art will appreciate that the invention includes other benzo[c]-chromen-6-one derivatives having anti-angiogenic, and/or anti-tumor activities. These characteristics can be determined for each derivative using the assays detailed below and elsewhere in the literature.

The process or processes by which benzo[c]chromen-6-one derivates affect cell growth remains to be fully researched, however, benzo[c]chromen-6-one derivates may induce changes in the levels and activities of various proteins involved in the progression of the cell cycle. These include cofactors of DNA replication and repair, e.g., proliferating cell nuclear antigen and cell division cycle kinases (and regulators). Benzo[c]chromen-6-one may also up-regulate Death Receptor 5 and caspase 8, inhibit HIF-1α (a global transcriptional regulator of angiogenesis genes), or inhibit the Akt/mTor signal transduction pathway (a key regulator pathway of cell growth and proliferation with its deregulation associated with human diseases, including but not limited to cancer).

Assays relevant to these mechanisms of action and inhibition of cell proliferation are well-known in the art. For example, anti-mitotic activity mediated by effects on tubulin polymerization activity can be evaluated by testing the ability of a benzo[c]chromen-6-one derivative to inhibit tubulin polymerization and microtubule assembly in vitro. Other such assays include counting of cells in tissue culture plates or assessment of cell number through metabolic assays or incorporation into DNA of labeled (radio-chemically, e.g., 3H-thymidine or fluorescently labeled) or immuno-reactive (BrdU) nucleotides. In addition, measuring HIF-α activity for example through luciferase reporter groups or Akt/mTor signalling through for example activated intermediates as in the phosphorylation of Akt. Furthermore, anti-angiogenic activity may be evaluated through endothelial cell migration, endothelial cell tubule formation or vessel outgrowth in ex-vivo models of rat aortic rings.

The present invention also relates to implants or other devices comprised of one or more compositions described herein or prodrugs thereof wherein the composition or pro-drug is formulated in a biodegradable or non-biodegradable format for sustained release. Non-biodegradable formats release the drug in a controlled manner through physical or mechanical processes without the format being itself degraded. Bio-degradable formats are designed to gradually be hydrolyzed or solubilized by natural processes in the body, allowing gradual release of the admixed drug or prodrug. Both bio-degradable and non-biodegradable formats and the process by which drugs are incorporated into the formats for controlled release are well known to those skilled in the art. These implants or devices can be implanted in the vicinity where delivery is desired, for example, at the site of a aberrant skin or in the vicinity of aberrant vasculature.

The present invention also relates to coated vascular stents to prevent restentosis, a re-narrowing or blockage of an artery at the same site where treatment, such as angioplasty or stent procedure, has already been done. According to the present invention, the stent or other surgically implantable device is coated with one or more compositions described herein. The coating of such a device is well known to those skilled in the art.

The present invention also relates to conjugated prodrugs and uses thereof. More particularly, the invention relates to conjugates of benzo [c] chromen-6-one derivatives and the use of such conjugates in the prophylaxis or treatment of conditions associated with uncharacteristic cell proliferation and/or uncharacteristic angiogenesis. Such diseases include, but are not limited to, excessive, abnormal stimulation or proliferation of cancer cells, endothelial cells or other pathologically involved cells.

The present invention also provides a conjugated prodrug of a benzo[c]chromen-6-one derivative conjugated to a biological activity modifying agent, e.g., a peptide, an antibody or fragment thereof, or in vivo hydrolysable esters, such as methyl esters, phosphate or sulfate groups, and amides or carbamates. Modifications can include modifying a hydroxyl group with a phosphate group. This derivative would not be expected to have activity due to the modification causing a significant change to the derivative thereby losing biological activity. However the modification imparts better solubility characteristics, i.e., more water soluble, which could facilitate transport through the blood or give it better oral availability to allow it to reach its site of activity. Once it gets into the microenvironment where it is needed to have activity, the modification is cleaved through natural processes, i.e., endogenous enzymes which are present at the site of needed activity. Alternatively it may just keep the derivative in a state to give it better systemic concentration which would then be cleaved again in the systemic circulation and thereby enhance its activity. The incorporation of benzo[c]chromen-6-one derivatives into a disease-dependently activated prodrug enables significant improvement of potency and selectivity in treating one or more disease conditions referred to hereinabove.

In addition to the compounds of the present invention, the pharmaceutical composition of this invention may also contain or be co-administered (simultaneously or sequentially) with one or more pharmacological agents of value in treating one or more disease conditions referred to hereinabove. Such agents include, but are not limited to, pharmaceutical agents well known to those skilled in the art for their oncolytic or anti-cancer activity. Other agents include those that suppress the side-effects of oncolytic or anti-cancer agents such as those directed toward counter-acting nausea and emesis.

Furthermore, the benzo[c]chromen-6-one derivatives or prodrugs thereof may be incorporated into bio-degradable or non-degradable formats allowing for sustained release. For example, the formulation being implanted in the proximity of where the delivery is desired, at the site of a tumor or in the vicinity of aberrant vasculature. Alternatively, the pharmaceutical formulation can be, packaged into a delivery vehicle that has a chemical moiety that provides for specificity. For example, the moiety can be an antibody or some other such molecule that directs and facilitates delivery of the active agent to the desirable site (or cell/tumor).

The present invention also relates to use of the benzo[c] chromen-6-one derivatives or prodrugs thereof for the preparation of a medicant for the prophylaxis or treatment of conditions associated with any disease characterized by uncharacteristic cell proliferation and-or uncharacteristic angiogenesis and/or inflammation.

The present invention also relates to the provision of a pharmaceutical composition comprising benzo[c]chromen-6-one derivatives or prodrugs thereof according to the present invention together with a pharmaceutical acceptable carrier, diluent or excipient.

The pharmaceutical composition may also be used for the prophylaxis or treatment of conditions associated with any disease characterized by uncharacteristic cell proliferation and/or uncharacteristic angiogenesis and/or inflammation.

The present invention also pertains to methods of prophylaxis or treatment of a condition associated with any disease characterized by uncharacteristic cell proliferation and/or uncharacteristic angiogenesis and/or inflammation, said method including administering to a subject in need of such prophylaxis or treatment an effective amount of benzo [c]chromen-6-one derivatives or prodrugs thereof according to the present invention as described hereinabove. (It should be understood that prophylaxis or treatment of said condition includes amelioration of said condition.)

By "effective amount" it is meant a therapeutically effective amount that relieves symptoms, partially or completely, associated with a particular disease or syndrome. Such amounts can be readily determined by an appropriately skilled practitioner, taking into account the condition to be treated, the route of administration, and other relevant factors—well known to those skilled in the art. Such a person will be readily able to determine a suitable dose, mode and frequency of administration.

Pharmaceutically acceptable salts of the benzo[c] chromen-6-one derivatives or prodrugs thereof may be prepared in any conventional manner. In vivo hydrolysable esters, for example, methyl esters, phosphate or sulfate groups, and amides or carbamates may be prepared in any conventional manner.

The benzo[c]chromen-6-one derivatives or prodrugs thereof can be provided as physiologically acceptable formulations using known techniques and these formulations can be administered by standard routes. The compositions may be administered through means including, but not limited to, topical, oral, rectal or parenteral, for example, intravenous, subcutaneous or intramuscular, route. In addition, the compositions may be incorporated into formats allowing for sustained release, the formats being implanted in the proximity of where the delivery is desired, for example, at the site of the skin disease or aging skin or in the vicinity of aberrant vasculature. The dosage of the composition will depend on the condition being treated, the particular derivative used, and other clinical factors such as weight and condition of the subject and the route of administration of the compound—all of which is appreciated by those skilled in the art. For example, a person skilled in the art will be able by reference to standard texts, such as Remington's Pharmaceuticals Sciences 17th edition (the entire teaching of which is incorporated herein by reference), determine how the formulations are to be made and how these may be administered.

The formulations including, but not limited to, those suitable for oral, rectal, nasal, inhalation, topical (including, but not limited to, dermal, transdermal, buccal and sublingual), vaginal or parenteral (including, but not limited to, subcutaneous, intramuscular, intravenous, intradermal, intraocular (including, but not limited to, intra-vitreal, sub-conjunctival, sub-Tenon's, trans-scleral), intra-tracheal and epidural) and inhalation administration. The formulations may be conveniently presented in unit dosage form and may be prepared by conventional pharmaceutical techniques. Such techniques include the step of bringing into association the active ingredient and a pharmaceutical carrier(s) or excipient(s). The formulations are prepared by uniformly and intimately bringing into association the active ingredient with liquid carriers or finely divided solid carriers or both, and then, if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optimally with one or more accessory ingredient. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for administration via the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical, cosmeceutical or cosmetic acceptable carrier. A viable delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, for example, by rapid inhalation through the nasal passage from a container of the powder held close up to the nose. Suitable formulations include wherein the carrier is a liquid for administration, as for example a nasal spray or as nasal drop, including aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostatic agents and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried, lyophilized, conditions requiring only the addition of the sterile liquid, for example, water for injections, immediately prior to use. Extemporaneous injection solution and suspensions may be prepared from sterile powders, granules and tablets of the kinds previously described.

Acceptable unit dosage formulations are those containing a daily dose or unit daily sub-dose, as herein above recited, or an appropriate fraction thereof of the administered ingredient.

In addition to the ingredients mentioned above, the formulations of the present invention may include other agents conventional in the art having regard to the type of formulation in question, for example, those suitable for oral administration may include flavoring agents.

The present invention includes compositions of about 100% to about 90% pure isomers. In another aspect, the invention pertains to compositions of about 90% to about 80% pure isomer. In yet another aspect, the invention pertains to compositions of about 80% to about 70% pure isomer. In still another aspect, the invention pertains to a composition of about 70% to about 60% pure isomer. In yet a further aspect, the invention pertains to a composition of about 60% to about 50% pure isomer. However, a steriochemical isomer labeled as alpha or beta may be a mixture of both in any ratio, where it is chemically possible by one skilled in the art. Additionally, included by this invention are both classical and non-classical bio-isosteric atom and substituent replacements and are well known by one skilled in the art. Such bio-isosteric replacements include, for example, substitution of =S or =NH for =O.

Known compounds that are used in accordance with the invention and precursors to novel compounds according to the invention can be purchased from commercial sources, for example, Sigma-Aldrich. Other compounds according to the invention can be synthesized according to known methods well known to those skilled in the art.

The synthetic route for benzo[c]chromen-6-one derivatives SG00292 and SG00392 are summarized in Scheme 1, infra. This synthetic route presents one potential way to prepare this series of derivatives, and other synthetic routes (including modifying the order of synthetic steps or reagents) are possible to someone skilled in the art. In specific cases, the nature of protecting groups or the order of reactions may have to be altered in order to reach the desired products. These changes to the general synthetic schemes are well understood to one skilled in the art.

EXAMPLES

Benzo[c]chromen-6-one derivatives according to the present invention may be prepared using the following reaction schemes, Scheme 1 and synthetic methods Scheme 2.

The present invention also includes benzo[c]chromen-6-one derivatives prepared from the starting point of Scheme 1. The synthesis of these analogs are described in the synthetic methods shown in Scheme 3 and represents examples from the benzo[c]chromen-6-one derivatives as depicted in Table 1.

Scheme 1

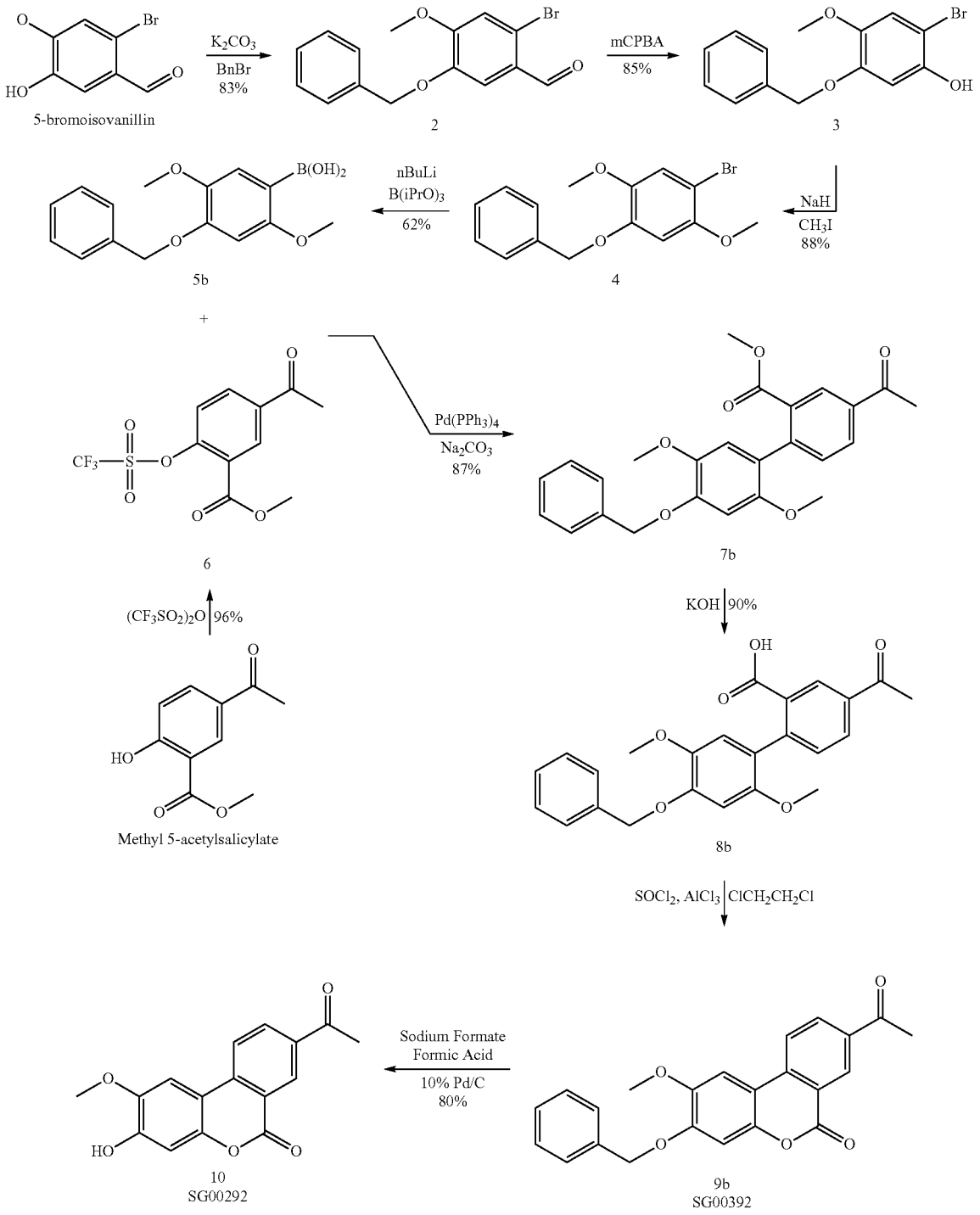

Scheme 2

Synthesis

5-Benzyloxy-2-bromo-4-methoxybenzaldehyde (2)

2-Bromo-5-hydroxy-4-methoxybenzaldehyde (25 g, 0.108 mol) and $K_2CO3$ (30 g, 0.216 mol) were added to acetonitrile (250 mL) and flushed with Ar. Benzyl bromide (20 g, 0.12 mol) was added and the mixture was heated under Ar for 20 h at 50° C. After cooling, the mixture was poured into water (200 ml) and extracted with $CH_2Cl_2$ (300 mL). The $CH_2Cl_2$ was washed with water (3×100 mL), dried and concentrated. Recrystallization with isopropanol: water (3:1) gave 28.8 g (83%) of 2 as a light brown solid. $^1$H-NMR (400 MHz, CDCl3) dH 3.96 (3H, s, $OCH_3$), 5.16 (2H, s, CH2Ph), 7.07-7.48 (7H, m, ArH+$CH_2$Ph), 10.16 (1H, s, CHO).

5-Benzyloxy-2-bromo-4-methoxyphenol (3)

5-Benzyloxy-2-bromo-4-methoxy-benzaldehyde 2 (5 g, 16.0 mmol) was added to CH2Cl2 (40 mL), flushed with Ar and cooled in an ice bath. A solution of mCPBA (5.2 g) in $CH_2Cl_2$ (50 mL) was added dropwise. Once the addition was complete the reaction mixture was refluxed under Ar for 14 h. After cooling the mixture was washed with sat. $NaHCO_3$ (3×50 mL), brine, dried and concentrated. The residue was recrystallized from ethyl acetate/hexanes to 4.1 g (85%) of 3 as large tan needles. $^1$H-NMR (400 MHz, CDCl3) dH 3.88 (3H, s, $OCH_3$), 5.10 (2H, s, $CH_2Ph$), 6.74 (1H, s, ArH), 7.08 (1H, s, ArH), 7.34-7.40 (5H, m, $CH_2Ph$), 8.25 (1H, s, OH).

1-Benzyloxy-4-bromo-2,5-dimethoxybenzene (4)

5-Benzyloxy-2-bromo-4-methoxy-phenol 3 (2.76 g, 89.0 mmol) and NaH (0.89 g, 13.0 mmol, 60% dispersion in oil) were added to a flask and flushed with Ar. Dry THF (50 mL) was added and the suspension was stirred in an ice bath for 20 min. $CH_3I$ (1.7 mL, 27.0 mmol, filtered through basic alumina) was added and the mixture stirred at room temperature under Ar for 18 h. After cooling the reaction mixture in an ice bath, water was added slowly. The mixture was extracted with ethyl acetate, dried and concentrated to give yellow oil that solidified under vacuum. The oil was purified by silica gel chromatography using silica gel with (10% ethyl acetate/hexanes) to give 2.5 g (88%) of 4 as a white solid. $^1$H-NMR (400 MHz, CDCl3) dH 3.75 (3H, s, $OCH_3$), 3.84 (3H, s, $OCH_3$), 5.15 (2H, s, $CH_2Ph$), 6.57 (1H, s, ArH), 7.07(1H,s, ArH), 7.32-7.42(5H,m,$CH_2Ph$).

4-Benzyloxy-2,5-dimethoxyphenylboronic acid (5b)

1-Benzyloxy-4-bromo-2,5-dimethoxybenzene 4 (7.48 g,23.0 mmol) was placed in a dry flask and flushed with Ar. Dry THF (75 mL) was added and the solution was cooled to −78° C. in a dry ice/acetone bath. nBuLi (11 mL, 2.5M in hexanes) was added and the mixture was stirred for 20 min at −78° C. Triisopropyl borate (10.7 mL, 0.463 mol) was added and the reaction stirred for 2 h at −78° C. then allowed to come to room temperature at which time a white precipitate began to form. After stirring for an additional 20 h the reaction was quenched with saturated $NH_4Cl$ (25 mL). After separating the organic layer the aqueous layer was extracted with ethyl acetate (2×50 mL). The organic layers were combined, dried and concentrated. The residue was triturated with hexanes and filtered to give 4.1 g (62%) of 5b as a light off-white creamy solid. $^1$H-NMR (400 MHz, DMSO-d6) dH 3.70 (3H, s, $OCH_3$), 3.79 (3H, s, $OCH_3$), 5.16 (2H, s, $CH_2Ph$), 6.77 (1H, s, ArH), 7.18 (1H, s, ArH), 7.33-7.52 (5H, m, $CH_2Ph$)

5-Acetyl-2-trifluoromethanesulfonyloxybenzoic acid methyl ester (6)

Methyl 5-acetylsalicylate (25.0 g, 0.129 mol) was dissolved in $CH_2Cl_2$ (250 mL) and pyridine (60 mL) under Ar at 0° C. Trifluoromethanesulfonic anhydride (37.9 g, 0.133 mol) was then added over 20 min. The reaction mixture was stirred for an additional 30 min and then quenched with water (500 mL). The organic layer was separated and washed three times with 5% HCl (80 mL). After removing the solvent the solid obtained was dried under vacuum to yield 40.3 g (96%) of 6. $^1$H-NMR (400 MHz, $CDCl_3$) dH 2.56 (3H, s, $COCH_3$), 3.89 (3H, s, $OCH_3$), 7.32 (1H, d, ArH), 8.12 (1H, d, ArH), 8.52 (1H, s, ArH), 4-Acetyl-4'-benzyloxy-2'-methoxybiphenyl-2-carboxylic acid methyl ester (7b)

4-Benzyloxy-2,5-dimethoxyphenylboronic acid 5b (4.15 g, 14.4 mmol), 5-Acetyl-2-trifluoromethanesulfonyloxybenzoic acid methyl ester 6 (4.69 g, 14.4 mmol) and $K_2CO_3$ (3.98 g, 28.8 mmol) were added and the flask was flushed with Ar. Absolute ethanol (83 mL) and DME (94 mL) were added followed by Pd $(PPh_3)_4$ (0.87 g, 0.785 mmol) and the reaction mixture refluxed for 4 h. After cooling, water (100 ml), ethyl acetate (100 mL) and brine (50 mL) were added. The organic layer was washed with brine (2×50 mL) and the combined aqueous fraction was back extracted with ethyl acetate. The combined organic fraction was dried, concentrated and recrystallized from ethyl acetate/hexanes to give 6.5 g (99%) of 7b as a yellow solid. $^1$H-NMR (400 MHz, CDCl3) dH 2.65 (3H, s, $COCH_3$), 3.58 (3H, s, $OCH_3$), 3.68 (3H, s, $OCH_3$), 3.88 (3H, s, $OCH_3$), 5.21 (21H, s, $CH_2Ph$), 6.55 (1H, s, ArH), 6.86 (1H, s, ArH), 7.30-7.48 (6H, m, ArH+$CH_2Ph$), 8.10 (1H, d, ArH),8.37(1H,s,ArH), 4-Acetyl-4'-benzyloxy-2'-methoxybiphenyl-2-carboxylic acid (8b)

To 4-Acetyl-4'-benzyloxy-2'-methoxybiphenyl-2-carboxylic acid methyl ester 7b (4.06 g, 9.7 mmol) and NaOH (0.773 g, 19.4 mmol) was added methanol (60 mL) and water (60 mL). The reaction was refluxed under Ar for 7 h then cooled to room temperature. After placing in an ice bath, 1 M HCl was added to give a yellow precipitate that was filtered, washed with water and recrystallized from THF/hexanes to give 2.7 g (69%) of 8b as yellow crystals. $^1$H-NMR (400 MHz, $CDCl_3$) dH 2.68 (4H, s, $COCH_3$), 3.62 (3H, s, $OCH_3$), 5.16 (2H, s, $CH_2Ph$), 6.77 (1H, s, ArH), 7.18 (1H, s, ArH), 7.33-7.52 (5H, m, $CH_2Ph$), 3.90 (3H, s, $OCH_3$), 5.22 (2H, S, $CH_2Ph$), 6.58 (1H, s, ArH), 6.90 (1H, s, ArH), 7.34-7.50 (6H, m, ArH+$Ch_2Ph$), 8.17 (1H, d, ArH), 8.50 (1H, s, ArH), 8-Acetyl-3-benzyloxy-2-methoxybenzo[c]chromen-6-one (9b)

4-Acetyl-4'-benzyloxy-2'-methoxybiphenyl-2-carboxylic acid 8b (1.0 g, 2.5 mmol) was suspended in 1,2-dichloroethane (30 mL). $SOCl_2$ (200 mL, 2.7 mmol) was added and the reaction mixture refluxed for 2 h under Ar. After cooling to room temperature (some precipitate formed) $AlC_{13}$ (0.262 g, 0.002 mol) was added turning the mixture red. The reaction was stirred at room temperature for 17 h then quenched with water (30 mL) and diluted with $CH_2Cl_2$ (100 mL). After washing the organic layer with brine (2×50 mL) it was dried and concentrated. The residue was dissolved in hot $CHCl_2$ and then cooled. Hexanes were added to help precipitate the product. A second recrystallization gave 0.3 g, (32%) of 9b as a yellow solid. $^1$H-NMR (400 MHz, $CDCl_3$) dH 2.73 (3H, s, $COCH_3$), 4.05 (3H, s, $OCH_3$), 5.28 (2H, s, $CH_2Ph$), 6.94 (1H, s, ArH), 7.35-7.50 (6H, s, ArH+$CH_2Ph$), 8.07 (1H, d, ArH), 8.42 (1H, d, ArH), 8.92 (1H, s, ArH)

8-Acetyl-3-hydroxy-2-methoxybenzo[c]chromen-6-one (10)

Sodium formate (2.18 g, 32 mmol) and formic acid (4.2 mL, 106.8 mmole) were added to a suspension of 9b (10.0 g, 26.71 mmol) in a 1:1 mixture of dry THF and absolute ethanol (1.5 L) in a 3 liter 3-necked flask equipped with an overhead stirrer and a heating mantle. To this mixture was added 100 mg of 10% palladium on carbon and the reaction refluxed under argon for 7 hours. At this time, all of the starting 9b had gone into solution. The solution was filtered hot to remove the catalyst and the solvent removed by rotary evaporation. (If the solution is allowed to cool down, the product will precipitate and can be separated from the catalyst by extracting the solid with 6 liters of refluxing methanol). The resulting solid (7.8 g) was purified by silica gel chromatography as described below.

In a typical run, 3.12 g of crude 10 was mixed with 20 g of silica gel, suspended in 200 mL of methanol and the solvent removed by rotary evaporation. This material was placed on top of a silica gel column (6 cm×36 cm, 400 g of silica gel), and eluted with a stepwise gradient of 1% acetone/dichloromethane, 10% acetone/dichloromethane and 100% acetone. All pure fractions were combined and evaporated to give 2.4 g (80% yield) of the desired intermediate 10. 1H (300 MHz) (DMSO-d6) d 2.07 (3H, s), 2.66 (3H, s), 3.92 (3H, s), 6.81 (1H, s), 7.78 (1H, s), 8.33 (1H, d, J=8.7 Hz), 8.46 (1H, d, J=8.7 Hz) and 8.66(1H, d, J=1.8 Hz).

Scheme 3

SG00393. SG00392 (1.0 g, 2.67 mmol) and NaBH4 (0.1 g, 2.67 mmol) were added to a 2:1 mixture of THF (20 mL) and absolute ethanol (10 mL) and left to stir for 1.5 h. The reaction mixture was cooled in an ice bath and 0.5 N HCl added until the color changed from yellow to clear. Water (20 mL) was added and the mixture extracted with CH2Cl2, dried, concentrated and the residue purified by silica gel flash column chromatography using CH2Cl2:acetone (8/1) to give 0.71 g of SG00393.

SG00394. SG0093 (0.1 g, 0.27 mmol) was added to anhydrous CH2Cl2 (6 mL) and cooled to −78° C. giving a heterogeneous mixture. DIBAL (1M in hexanes, 0.66 mL, 0.66 mmol) was added dropwise over 2 h. An additional amount of DIBAL was added (0.2 mL) and after a total time of 2.5 h the reaction was quenched by the addition of methanol (0.8 mL). The reaction mixture was allowed to come to room temperature, CH2Cl2 (100 mL), ice and a small amount of acetone were added and the mixture stirred for 15 min. The CH2Cl2 layer was washed with st NaHCO3, brine, dried and concentrated. The residue was re-dissolved in acetone (40 mL) and pre-adsorbed onto silica gel (1 g). After evaporation of the acetone the residue was purified by silica gel flash column chromatography using CH2Cl2: acetone (6/1) to give 69 mg of SG0094.

SG000395. Crude SG00394 (1.18 g, 3.12 mmol), triethylamine (1.73 mL, 12.5 mmol), acetic anhydride (1.18 mL, 12.5 mmol) and anhydrous CH2Cl2 (50 mL) were stirred at room temperature under N2. Once crystal of DMAP was added, the reaction mixture stirred for 15 min, then extracted with CH2Cl2. The CH2Cl2 layer was washed with sat NaHCO3, brine, dried, concentrated and purified by silica gel flash column chromatography using CH2Cl2:acetone (10/1) to give 0.89 g of SG800399.

SG00396. SG00395 (0.83 g, 0.197 mmol) was added to anhydrous CH2Cl2 (25 mL) and cooled in a methanol/dry ice bath under N2. Et3SiH (0.631 mL, 3.95 mmol) was added followed by BF3 Et2O (0.375 mL, 2.96 mmol) dropwise and stirred vigorously for 0.5 h. The reaction mixture was removed from the cooling bath and after 45 minutes quenched with sat NaHCO3 (3 mL). The reaction mixture was extracted with CH2Cl2, washed with sat. NaHCO3, brine, dried, concentrated and purified by silica gel flash column chromatography using ethyl acetate: hexanes (1/2) to give 0.71 g of SG00396.

SG00397. SG00396 (0.135 g, 0.334 mmol), formic acid (0.525 mL, 1.34 mmol), sodium formate (27 mg, 0.4 mmol), 10% Pd/C (0.3 mol %), anhydrous THF (4 mL) and absolute ethanol (4 mL) were heated to reflux under N2 for 1.5 h. The reaction was cooled and approximately half of the reaction mixture evaporated. The silica gel residue was purified by silica gel flash column chromatography using ethyl acetate: hexanes (1/2) to give 50 mg of SG00397.

SG00398. To the remaining half of the reaction mixture in the preparation of SG00397 was added additional 10% Pd/C and the reaction refluxed for 0.5 h. The Pd/C was filtered off, washed with methanol and silica gel added to the filtrate. After concentrating, the silica gel residue was purified by silica gel flash column chromatography using ethyl acetate: hexanes (1/2) to give 32 mg of SG00398.

SG00399. SG00395 (0.44 g, 1.09 mmol) and Amberlyst-15 resin (12-15 beads) were stirred in methanol (10 mL) under N2 for 2 h. The Amberlyst was filtered, washed with methanol and the filtrate concentrated. The residue was purified by silica gel flash column chromatography using ethyl acetate:hexanes (1/2) to give 0.4 g of SG00399.

SG00400. SG00397 (95 mg, 0304 mmol) was added to methanol (2 mL). To this mixture K2CO3 (0.126 g, 0.912 mmol) and water (0.1 mL) were added and the reaction stirred under N2 for 3 h. The reaction was stopped by the addition of 1% HCl (0.1 mL) and methanol (10 mL). Silica gel was added, the solvent evaporated and the residue was purified by silica gel flash column chromatography using ethyl acetate: hexanes (1/1) to give 72 mg of SG0400.

SG00477. SG00292 (0.18 g, 0.63 mmol) was added to anhydrous CH2Cl2 (7 mL) with stirring under N2. Et3N (0.35 mL, 2.53 mmol), acetic anhydride (0.24 mL, 2.53 mmol) and one crystal of DMAP were added. After stirring for 15 min. CH2Cl2 was added and the mixture washed with sat NaHCO3, brine, dried, concentrated and pre-adsorbed onto silica gel. The silica gel flash column chromatography using ethyl acetate:hexanes (2/1) to give 80 mg of SG0477.

SG00490. SG00396 (122 mg, 0.3 mmol), K2CO3 (125 mg, 0.9 mmol) and water (0.13 mL) were added to methanol (3.3 mL) and stirred under N2 for 1.5 h then quenched with 1% H2SO4. The reaction was extracted with CH2Cl2 and divided into two equal portions. One portion was concentrated and purified by silica gel flash column chromatography using ethyl acetate:hexanes (1/1) to give 48 mg of SG00490. The remaining portion was converted to SG00491.

SG00491. The remaining portion of crude SG00490 was oxidized using the Dess-Martin reagent (37.3 mg, 0.9 mmol) over 1 h. The reaction was extracted with CH2Cl2, washed with sat NaHCO3, brine, dried, concentrated and purified by silica gel flash column chromatography using ethyl acetate: hexanes (1/1) to give 40 mg of SG00491.

SG00492. Prepared following the method for SG00392 starting with SG00491. Yield 44 mg.

SG00493. SG492 (116 mg, 0.41 mmol), K2CO3 (112 mg, 0.82 mmol) and CH3I (1 mL) were added to acetone (10 mL) and refluxed for 2 days. Silica gel was added to the reaction mixture, concentrated and purified by silica gel column chromatography using silica gel flash column chromatography using CH2Cl2:acetone (9/1) to give 100 mg of SG00493.

SG00494. Prepared following method for SG00493 using 1-(2-chloroethyl)piperidine hydrochloride. Yield 52 mg.

SG00495. Prepared following method for SG00493 using ethyl bromide. Yield 20 mg.

SG00496. SG00393 (116 mg, 0.308 mmol) was added to anhydrous THF (10 mL) in an ice bath. NaH (60% dispersion in oil, 22 mg, 0.92 mmol) was added and the mixture stirred for 20 min. CH3I was added dropwise and the reaction stirred for 0.5 h. The ice bath was removed and the reaction was stirred overnight. Additional CH3I was added and the reaction mixture refluxed for 5 h. The reaction was quenched with water and distilled to remove the excess CH3I. CH2Cl2 and water were added, and after separating, the CH2Cl2 layer was dried, concentrated and purified by silica gel flash column chromatography using ethyl acetate: hexanes (1/1) to give SG00496.

SG00510. Prepared following the method for SG00393 using SG00493. Yield 48 mg.

SG00511. Prepared following the method for SG00493 using 2-(bromomethyl) hydrobromide. Yield 170 mg.

SG00512. Prepared following the method for SG00493 using ethyl bromide. Yield 63 mg.

SG00513. Prepared following the method for SG00493 using isopropyl bromide. Yield 220 mg.

SG00514. Prepared following the method of SG00493 using 7-hydroxycourmarin and benzyl bromide. Yield 1.3 g.

SG00519. Prepared following the method for SG00493 using scopoletin and benzyl bromide. Yield 17 mg.

SG00520. Prepared following the method for SG00393 using SG00494. Yield 75 mg.

SG00521. Prepared following the method for SG00393 using SG00512. Yield 118 mg.

SG00526. SG00511 (50 mg, 0.133 mmol) and NaBH4 (5.0 mg 0.133 mmol) were added to a 1:1 mixture of ethanol and THF. (10 mL total) and left to stir for 48 h, then refluxed for 2 h. After cooling the reaction mixture was acidified to pH 2 with 1 N HCl then taken to pH 8 with sat NaHCO3 and extracted with ethyl acetate (3×20 mL). The combined organic layers were washed with water, brine, dried and concentrated. The residue was purified by silica gel chromatography using a gradient of hexanes:CHCl3 (1/1) following by CHCl3 following by 3% CH3OH/CHCl3 to give 40 mg of SG00526.

SG00527. SG292 (100 mg, 0.35 mmol) was added to a mixture of NaH (15.4 mg, 0.4 mmol) in DMF (10 mL) and the reaction mixture refluxed for 2 h. After cooling down to room temperature 4-methoxybenzyl bromide (0.57 mL, 0.42 mmol) dissolved in DMF was added and the reaction mixture heated to 70° C. for 9 h. Water (10 mL) was added and the reaction mixture extracted with CHCl3 (3×20 mL), the combined organic layers were washed with water, brine, dried and concentrated. The residue was purified by hexanes:CHCl3 (1/2) followed by CHCl3 to give 85 mg of SG00527.

SG00528. Prepared following, method for SG00526 using SG00530. Yield 20 mg.

SG00529. Prepared following method for SG00526 using SG00527. Yield 40 mg.

SG00530. Prepared following method for SG00527 using 3-methoxybenzyl bromide. Yield 110 mg.

SG00531. Prepared following method for SG0093 using SG00495. Yield 36 mg.

SG00532. Prepared following method for SG00393 using SG0513. Yield 71 mg.

SG00533. Prepared following method for SG00393 using SG00273. Yield 8 mg.

SG00541. Prepared following method for SG00527 using 2-methoxybenzyl chloride. Yield 80 mg.

SG00542. Prepared following method for SG00527 using 2-(chloromethyl)phenyl acetate. Yield 80 mg.

SG00543. To SG00392 (0.19 g, 0.51 mmol) in anhydrous CH2Cl2 (8 mL) was added CH3MgI (0.2 mL, 1.6 mM) dropwise with stirring at room temperature under N2. After 25 min additional CH3MgI (0.2 mL, 1.6 mM) was added. After 1 h still additional CH3MgI (0.2 mL, 1.6 mM) was added. The CH2Cl2 was separated, washed with slightly acidic water, silica gel added and the CH2Cl2 evaporated to pre-adsorb the crude reaction. The dimethyl alcohol was purified by silica gel flash column chromatography using ethyl acetate:hexanes (2/1) and used in the next step. The dimethyl alcohol (58 mg, 0.15 mmol) was debenzylated following the method for SG00292 to give SG00543. Yield 32 mg.

SG00544. Prepared following method for SG00526 using 2-chloromethylphenyl acetate. Yield 15 mg.

SG00545. Prepared following method for SG00526 starting with SG00541. Yield 40 mg.

SG00546. Prepared following method for SG00527 using 3,5-dimethoxybenzyl chloride. Yield 80 mg.

SG00547. Prepared following method for SG00526 starting with SG00546. Yield 30 mg.

SG00548. The dimethyl alcohol (56 mg, 0.14 mmol) produced in the preparation of SG00543 was added to anhydrous CH2Cl2 (3 mL) containing a catalytic amount of Amberlyst-15 and MgSO4 and stirred for 6 h and then placed in the freezer overnight. After filtering, the crude dehydration product was purified by silica gel flash column chromatography using ethyl acetate:hexanes (1/2) and used in the next step. The purified dehydration product was dissolved in absolute ethanol (3 mL) and a suspension of 10% Pd—C (30 mg) in absolute ethanol (1.5 mL) was added and a balloon filled with H2 attached. After stirring for 7 h the catalyst was filtered off, the crude reaction pre-adsorbed onto silica gel and purified by silica gel flash column chromatography using ethyl acetate: hexanes (1/2) to give SG00548.

SG00549. To a suspension of NaH (0.02 g, 0.55 mmol) in anhydrous DMF (5 mL) was added SG00391 (0.1 g, 0.37 mmol). The resulting yellow opaque mixture was refluxed for 1 h. Benzyl bromide (0.05 ml, 0.41 mmol) was added and the mixture became an orange/yellow clear solution. The reaction mixture was cooled added to water (15 mL) and extracted with ethyl acetate (3×12 mL). The organic layer was washed with brine, dried, concentrated and purified by flash silica gel chromatography using 15% ethyl acetate in hexanes to give SG00549 in a quantitative yield.

SG00550. Prepared following method for SG00549 using 4-methoxybenzyl bromide. Yield 100 mg.

SG00551. Prepared following method for SG00549 using 2-methoxybenzyl bromide. Yield 62 mg.

SG00552. Prepared following method for SG00549 using 3-methoxybenzyl bromide. Yield 70 mg.

SG00553. Prepared following method for SG00526 starting with SG00555. Yield 20 mg.

SG00554. Prepared following method for SG00526 starting with SG00556. Yield 24 mg.

SG00555. Prepared following method for SG00527 using 3-chloromethylpyridine hydrochloride. Yield 53 mg.

SG00556. Prepared following method for SG00527 using 4-chloromethylpyridine hydrochloride. Yield 45 mg.

SG00557. Prepared following method for SG00527 using 4-(chloromethyl)phenyl acetate. Yield 5 mg.

SG00558. Prepared following method for SG00527 using 4-(chloromethyl)phenyl. Yield 45 mg.

SG00559. Prepared following method for SG00527 using 4-methylbenzyl bromide. Yield 58 mg.

SG00560. Prepared following method for SG00549 using 4-bromobenzyl bromide. Yield 60 mg.

SG00561. Prepared following method for SG00549 using 3-bromobenzyl bromide. Yield 100 mg.

SG00562. Prepared following method for SG00549 using 3-chlorobenzyl bromide. Yield 80 mg.

SG00568. Prepared following method for SG00527 using 2-bromoethyl benzene. Yield 18 mg.

SG00569. Prepared following method for SG00543 using PhMgBr. Yield 19 mg.

SG00570. Prepared following the preparation of the dehydration product in the synthesis of SG00549 using the diol side product generated in the preparation of SG00549. Yield 21 mg.

SG00571. Prepared following method for SG00549 using 4-chlorobenzyl bromide. Yield 90 mg.

SG00572. Prepared following method for SG00549 using 4-flurobenzyl bromide. Yield 110 mg.

SG00573. Prepared following method for SG00549 using methyl 4-(bromomethyl)benzoate. Yield 40 mg.

SG00574. Prepared following method for SG00549 using 4-bromomethyl benzophenone. Yield 30 mg.

SG00575. Prepared following method for SG00526 starting with SG00559. Yield 25 mg.

SG00576. Prepared following method for SG00527 using 3-methylbenzyl bromide. Yield 30 mg.

SG00577. Prepared following method for SG00527 using 3,4,5-trimethoxybenzyl bromide. Yield 45 mg.

SG00592. Prepared following method for SG00527 using 4-methoxybenzyl chloride and 3-)4-bromophenyl)-7-hydroxycoumarin. Yield 62 mg.

SG00593. Prepared following method for SG00592 using 3,5-dimethoxybenzyl bromide. Yield 74 mg.

SG00594. Prepared following method for SG00527 using 4-trifluromethylbenzyl chloride. Yield 22 mg.

SG00595. Prepared following method for SG00527 using 4-fluorobenzyl chloride. Yield 43 mg.

SG00596. Prepared following method for SG00549 using 3,5-dimethoxybenzyl bromide. Yield 30 mg.

SG00597. Prepared following method for SG00527 using ethyl bromoethyl acetate. Yield 15 mg.

SG00598. Prepared following method for SG00527 using SG00293 (the ketone of SG00292 reduced to the alcohol). Yield 16 mg.

SG00599. From the reaction to prepare SG00569, SG00599 was also isolated. Yield 3.3 mg.

SG00609. Prepared following method for SG00526 starting with SG00577. Yield 32 mg.

SG00612. SG00292 (0.1 g, 0.35 mmol) was added to anhydrous CH2Cl2 (10 mL) with stirring. Pyridine (0.05 mL) and benzoyl chloride (0.1 mL) were added and the reaction stirred for 1 h. The reaction was poured into 5% HCl, extracted with CH2Cl2, washed with sat NaHCO3, dried, concentrated and purified by flash silica gel chromatography using ethyl acetate:hexanes (1/1) to give 25 mg of SG00612.

SG00613. Prepared following method for SG00612 using 4-methoxybenzyl chloride. Yield 2.3 mg.

SG00614. SG00547 (50 mg, 0.114 mmol) was dissolved in a 1:1 mixture of anhydrous diethyl ether and CH2Cl2 (6 mL). PBr3 (124 mg, 0.46 mmol) was added and the reaction stirred over the weekend at room temperature. Sat NaHCO3 was added and the reaction extracted with CH2Cl2, washed with brine, dried, concentrated and purified by flash silica gel chromatography using hexanes then CHCl3 then 1% methanol in CHCl3 to give 20 mg of SG00614.

SG00615. Prepared following the method for SG00543 starting with SG00546 and EtMgBr. Yield 55 mg.

SG00616. Prepared following the method for SG00543 starting with SG00546 and CH3MgI. Yield 74 mg.

SG00617. Prepared following method for SG00527 using SG00293 (the ketone of SG00292 reduced to the alcohol) and 4-bromomethyl benzophenone. Yield 13 mg.

SG00618. 4-benzyloxybenzoic acid (1 g, 4.4 mmol) was added to anhydrous CH2Cl2 (11 mL). A catalytic amount of DMF (5 drops) was added along with oxalyl chloride in CH2Cl2(2M, 5.75 mL) and the reaction stirred for 2 h. The solvents were evaporated and the crude 4-benzyloxybenzoyl chloride was used directly. SG00618 was prepared following the method for SG00612 using 4-benzylbenzoyl chloride. Yield 49 mg.

SG00619. Prepared following the method of SG00527 but using SG00293 (the methyl ketone of SG00292 reduced to the alcohol) and 4-formylbenzyl bromide (prepared by DIBAL reduction of 4-cyanobenzyl bromide. Yield 45 mg.

SG00620. Prepared following the method for SG00527 using 4-nitrobenzyl bromide. Yield 20 mg.

EXPERIMENTAL DATA

The following examples refer to representative illustrations from the compounds depicted in Table I. The aforementioned compounds are found to have anti-proliferative, anti-angiogenic properties and/or other meaningful activities to be described below.

Example 1

Anti-tumor (anti-proliferative for cancer cells), anti-angiogenic activity (anti-proliferative for endothelial cells) measured in vitro as inhibition of proliferation binding to estrogen receptor alpha and beta HUVEC Proliferation. Inhibition of the proliferation of human umbilical vein endothelial cells, HUVECs, is shown as one measure of anti-angiogenic activity. HUVECS and the required media complements were purchased from Cascade Biologics (Portland, Oreg.) and the growth and maintenance of the cultures was as described by the manufacturer. The proliferation assay was carried out by seeding the HUVECs in 96-well plates at a density of 1,000 cells/well in complete medium. Following a 24 h plating period, the cells were starved for 24 h in 0.5% serum before being treated with SG ("Signal Gene" now "Palomid") angiogenic inhibitors in the presence of 10 ng/ml b-FGF or dosing ranging presence of either b-FGF or VEGF in complete medium. After 48 h, cell number was determined using a calorimetric method as described by the supplier (Promega Corp., Madison, Wis.). The results were expressed as the percentage of the maximal b-FGF or VEGF response in the absence of angiogenic inhibitors. Non-proliferating endothelial cells were assayed by growing HUVECs to quiescence in 96-well plates and treating with angiogenic inhibitors for 48 h. Initially, 5,000 cells/well were seeded and confluence was achieved the next day. The plates were incubated another 24 h to ensure growth arrest before treatment with angiogenic inhibitors. Cell number was determined as outlined above.

Cancer Cell Lines. Measurement of the inhibition of tumor cell growth is one measure of anti-cancer activity. Two human cancer cell lines were used to assess the effects of SG angiogenic inhibitors on the proliferation of these cells. The cell lines were MCF-7 breast cancer cells and the colon carcinoma cell line, HCT-116. All cell lines were obtained from Americans Type Tissue Culture (Manassas, Va.) and maintained in their respective media as described by the supplier. The proliferation studies were carried out essentially as described for the proliferating endothelial cells.

ER Binding Assay. Derivatives which bind and transduce a signal through estrogen receptors would not be considered a positive activity as such an activity could enhance cancer growth as well as induce angiogenesis. Derivatives which either have little or no binding to estrogen receptors ("ER") would be one desired activity. Alternatively, derivatives which bound to estrogen receptors but did not transduce a signal could also be considered a positive activity. Human cDNAs encoding ERa and ERb were used as templates to express receptor proteins in vitro. The proteins were produced with rabbit reticulocyte lysates as supplied by Promega (TNT kit) that couples transcription and translation in a single reaction. The amount of template used in each reaction was determined empirically and expression was monitored in parallel reactions where [35S]methionine was incorporated into the receptor followed by gel electrophoresis and exposure to film. Binding reactions were carried out in 100 mL final volumes in TEG buffer (10 mM tris, pH 7.5, 1.5 mM EDTA, 10% glycerol). Five (5) mL of in vitro transcribed-translated receptor was used in each binding reaction in the presence of 0.5 nM [3H]estradiol (E2). All compounds were routinely tested from 10-11 M to 10-6 M and were diluted in ethanol. The reactions were incubated at 4° C. overnight and bound E2 was quantified by adding 200 mL dextran-coated charcoal. After a 15 min rotation at 4° C., the tubes were centrifuged for 10 min and 150 mL of the supernatant was added to 5 mL scintillation cocktail for determination of cpms by liquid scintillation counting. Controls for background were included in each experiment using 5 mL unprogrammed rabbit reticulocyte lysate. This value, typically 10-15% of the maximal counts was subtracted from all values. The maximum binding was determined by competing bound E2 with only the ethanol vehicle. This value was set to 100% (maximal E2 binding). Values for percent inhibition were calculated based on the maximal E2 binding. The data were plotted and Ki values calculated using the Prism Software. Experiments were conducted at least three times in duplicate.

The results are shown in Table II and FIG. 1. Activity of derivatives show anti-angiogenic activity through inhibition of the proliferation of angiogenic cytokine stimulated endothelial cells. The majority of the derivatives lack the ability to bind to estrogen receptors alpha and beta hence would not be expected to signal through these receptors, a possible stimulator of angiogenesis.

Activity of derivatives falls into two groups, those which have dual anti-tumor and anti-angiogenic activity and those which have primarily anti-angiogenic activity. See Table II below.

TABLE II

| Palomid | HUVECp % inhibition 3 mM | HUVECp % inhibition 0.3 mM | HUVECq % inhibition 3 mM | Colon % inhibition 3 mM | Breast % inhibition 3 mM | hERa % binding | hERb % binding |
|---|---|---|---|---|---|---|---|
| 529 | 113 | 65 | 31 | 20 | 32 | na | na |
| 547 | 106 | 42 | 25 | 17 | 35 | na | na |
| 575 | 104 | 41 | 33 | 10 | 31 | na | na |
| 545 | 100 | 32 | 22 | 21 | 17 | na | na |
| 528 | 80 | <10 | 25 | 11 | 16 | 41 | 31 |
| 550 | 77 | nd | 14 | <10 | 28 | na | na |
| 574 | 74 | 13 | 29 | 24 | na | na | na |
| 393 | 71 | nd | 21 | 26 | 11 | na | na |
| 551 | 62 | nd | na | na | 25 | na | na |
| 573 | 145 | nd | <10 | <10 | na | na | na |
| 546 | 100 | 18 | 23 | na | 13 | na | na |
| 559 | 96 | 72 | 35 | na | 17 | na | na |
| 568 | 78 | nd | 14 | na | <10 | na | 37 |
| 560 | 53 | nd | na | na | na | na | na |

na, no activity, HUVECp, HUVEC proliferating; HUVECq, HUVEC quiescent; hERa, human estrogen receptor alpha; hERb, human estrogen receptor beta

Example 2

Apoptotic Activity of Derivatives

Figure 2:
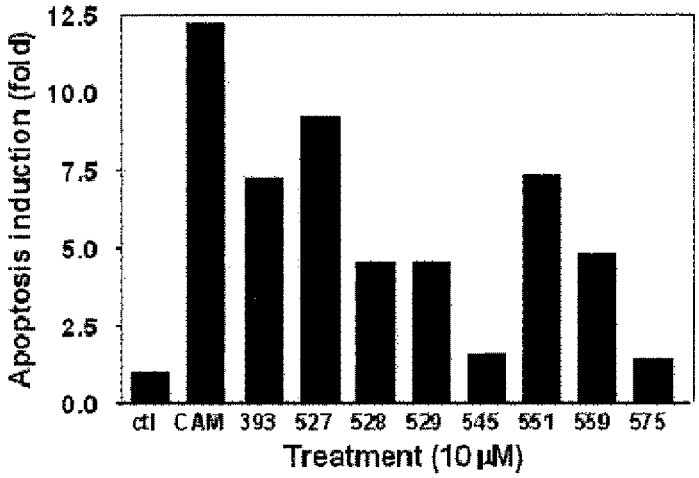
FIG. 2 is a bar graph presenting data on the apoptotic inducing ability of compounds of the present invention.
Figure 3:
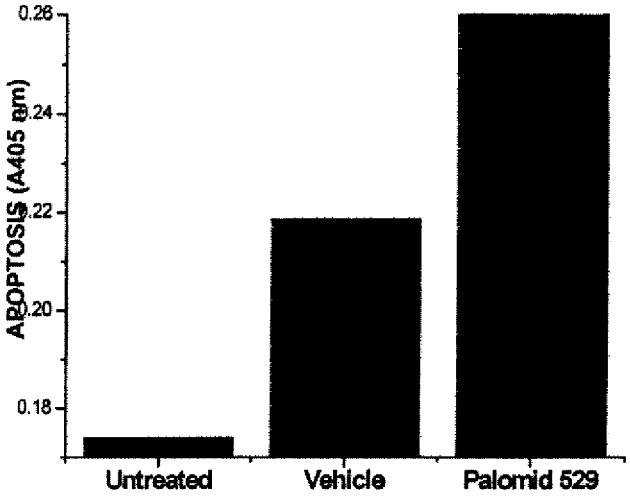
FIG. 3 is a bar graph presenting data on the apoptotic inducing activity in keratinocytes.

Apoptosis Assay. The apoptosis assay was conducted to determine if the derivatives inhibited cellular proliferation by inducing programmed cell death. Representative apoptotic activity is shown for endothelial cells with activity implied for other proliferating cells such as keratinocytes. Apoptosis of endothelial cells is yet another means to show anti-angiogenic activity. Cell death is monitored by quantifying the amount of cytoplasmic histone-associated DNA fragments that accumulate in the cell. Apoptosis assay kit was supplied by Roche (cat #1 544 675) with ELISA detection and a monoclonal antihistone antibody. Briefly, HUVECs or keratinocytes were trypsinized, diluted, and aliquoted into microfuge tubes at a concentration of 50,000 cells/tube. Treatment with a compound was for six hours at 37° C. followed by cell lysis and analysis using the detection kit according to the manufacturer. Apoptosis was quantified calorimetrically at an absorbance of 405 nm. Controls consisted of a negative vehicle (ctl) control (1% ethanol) and a positive camptothecin (CAM) control at 4 mg/mL in ethanol. See FIG. 2. For keratinocyte assay, Palomid 529, a leading clinical candidate available from Paloma Pharmaceuticals, was added at 100 μM. Results are shown in FIG. 3. (Palomid 529 is "SG00529", see Table I).

Example 3

Anti-Keratinocyte Activity Measured in Vitro as Inhibition of Proliferation of Keratinocytes and Induction of Apoptosis Skin diseases at least in part are due to abnormal presence and proliferation of keratinocytes. Means to either inhibit said keratinocyte proliferation and/or the ability to induce apoptosis of keratinocytes in said diseases would be expected to aid in the amelioration of abnormal skin pathologies. The following represents illustrative data to support this supposition.

Figure 4:
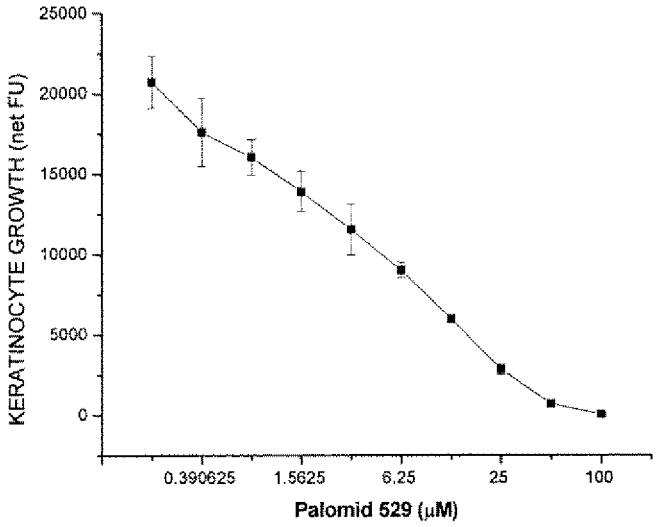
FIG. 4 is a graph showing inhibition of keratinocyte growth.

Keratinocyte proliferation. A benzo[c] chromen-6-one derivative, Palomid 529, was examined with the following protocol. Low passage human keratinocytes (NHEK, neonatal-pooled, p3-5, Cambrex, CC2507) were seeded in black 96-well plates at 1,000 cells per well in complete media (KBM, Cambrex) and incubated overnight. Cell culture media was then removed and replaced with fresh growth media plus either Palomid 529 or vehicle (1% DMSO). Palomid 529 was examined at nine concentrations (1:2 dilutions starting at 100 μM). Each experimental and control group was examined in replicates of six. Cultures were maintained for 3 days and cellular proliferation was then analyzed by determining metabolically active cells with a fluorescence-based assay (Alamar Blue, Invitrogen, diluted 1:20 in growth media, read following a five hour incubation, 530ex/580em). See FIG. 4.

Figure 5:
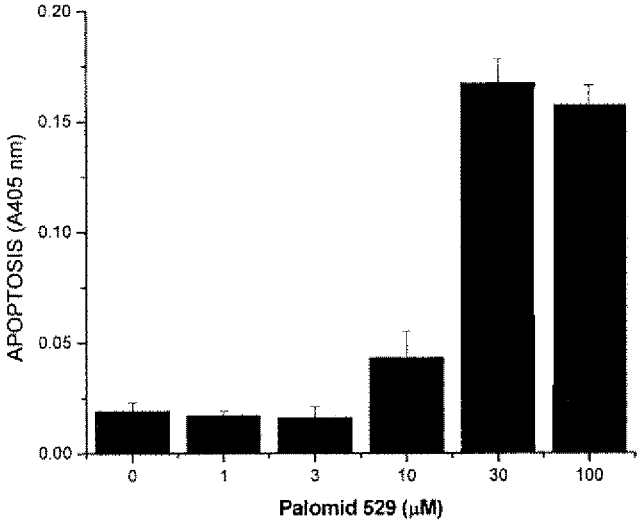
FIG. 5 is a bar graph showing induction of apoptotic activity at varying concentrations of compound.

Keratinocyte apoptosis. Palomid 529 was examined with the following protocol. Low passage human keratinocytes (NHEK, neonatal-pooled, p3-5, Cambrex, CC2507) were seeded in black 96-well plates at 3,000 cells per well in complete media (KBM, Cambrex) and incubated overnight (same plate as cell viability assay, adjacent wells). Cell culture media was then removed and replaced with fresh growth media plus either Palomid 529 or vehicle (1% DMSO). Palomid 529 was examined at seven concentrations (100, 30, 10, 1, 0.3, 0.1, & 0.03 μM). Each experimental and control group was examined in replicates of three. Following an overnight incubation, culture media was removed and the cells lysed with lysing reagent supplied with the Roche Cell Death ELISA plus kit. Lysed cells were then transferred to clean eppendorf tubes and centrifuged at 200×g to remove nuclei and cell debris. Supernatants, containing the cytoplasmic fraction (including cytoplasmic nucleosomes), were then transferred to streptavidin coated plates and incubated with anti-Histone (biotin conjugated) and anti-DNA (POD conjugated) antibodies for two hours. Wells were then carefully washed. ABTS was then added to the wells and following the development of color (approximately 30 minutes), the reaction stopped by the addition of ABTS Stop solution. Apoptosis was then measured by reading the OD at 405 nm with a reference background wavelength of 490 nm. See FIG. 5.

Example 4

Metabolic Stability Assay Using Human Primary Hepatocytes

Figure 6:
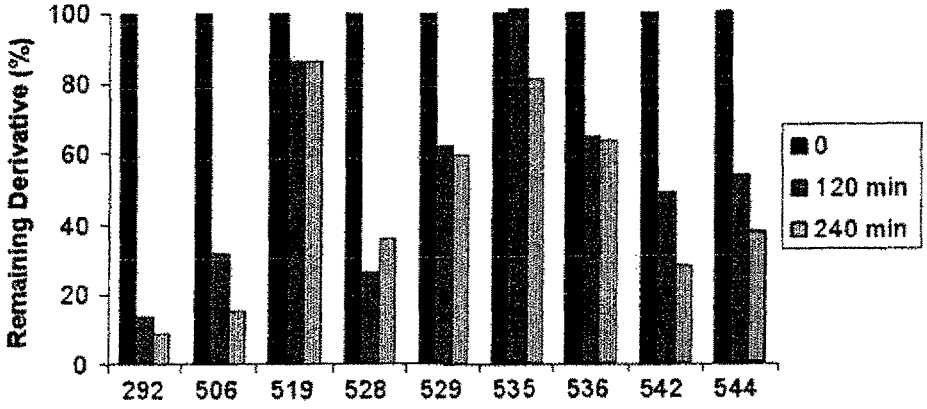
FIG. 6 is a bar graph showing metabolic stability of compounds of the present invention.

The cell based assay serves to determine the stability or half-life of compounds in cells. These specialized hepatocytes contain all of the necessary phase I and phase II enzymes that can act upon drugs. Compounds that are not or hardly metabolized in these cells are thought to be metabolically stable and would be expected to have a longer half-life in vivo than those that are metabolized by the hepatocytes. Results are shown in FIG. 6. Derivatives were incubated with human primary hepatocytes for 120 or 240 minutes. % remaining compound is shown at left. Control derivative capable of metabolism by phase I and/or phase II enzymes is shown as derivative 292.

What is claimed is:

1. A composition comprising a compound according to Formula I:

(I)

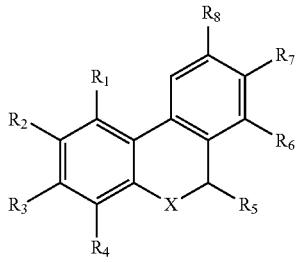

wherein,

R1 is H or alkyl;

R2 is [H,] OH, O-alkyl, amino, O-heterocyc, O-aryl, O—Ac, O—PO3, O—SO3, OSO2NH2 or O-substituted alkyl wherein said substitution is halo, aryl, or heteroaryl;

R3 is [OH,] O—CH2Aryl, O—CH2heteroaryl, *or* O-alkylaryl[, or O-acyl];

R4 is H, Alkyl, CH2Aryl, substituted alkyl, OH, O-alkyl, O-aryl, OCH2Aryl, OCH2Heteroaryl, O-Acyl, OPO3, OSO3, or OSO2NH2;

R5 is H, Oxo, aryl, hydroxyl, [alkyl,] or O-alkyl;

R6 is H;

R7 is H, Acyl, alkyl, O-alkyl, substituted alkyl wherein said substitution is hydroxyl or sulfamoyl, or O-substituted alkyl wherein said substitution is O—PO3 or OSO3;

R8 is H; and

X is O, N, or S[; and wherein if R3 is OH or O-acyl then R7 is Acyl, alkyl, or substituted alkyl wherein said substitution is hydroxyl]*;*

*and wherein said compound according to Formula I is selected from the group consisting of*

*SG00393*

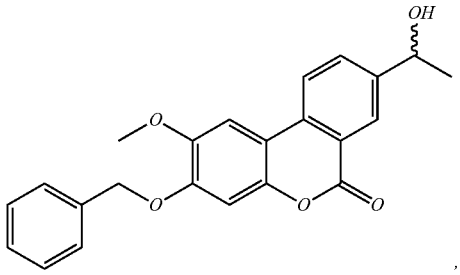

,

*SG00527*

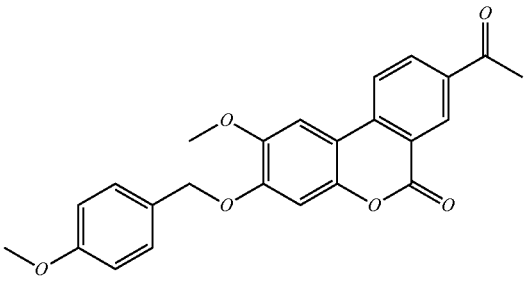

,

-continued
SG00528
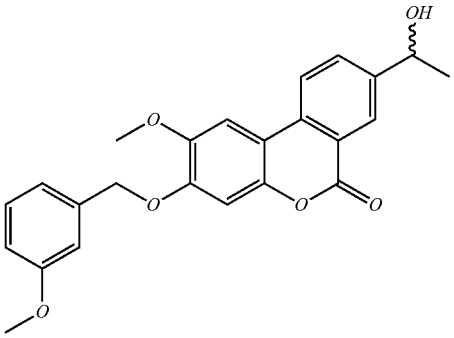
SG00529
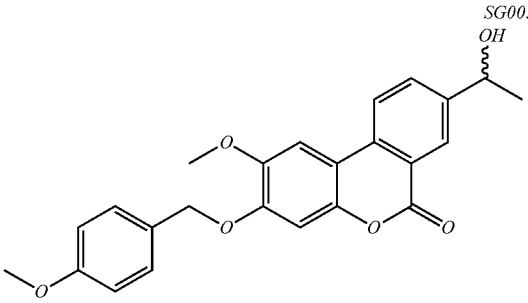
SG00545
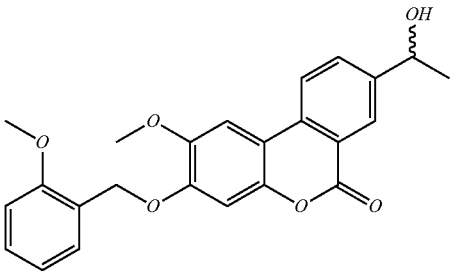
SG00546
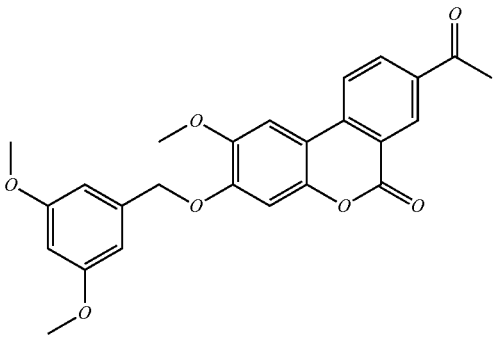
-continued
SG00547
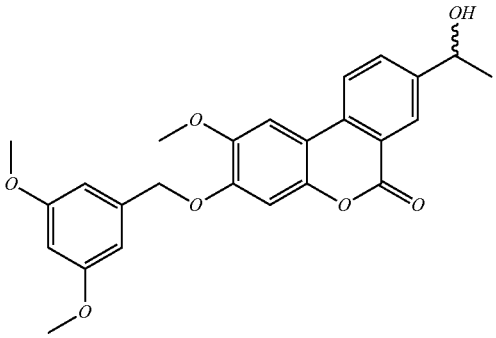
SG00550
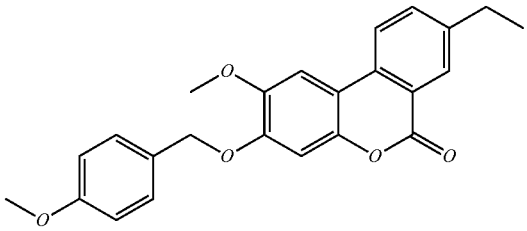
SG00551
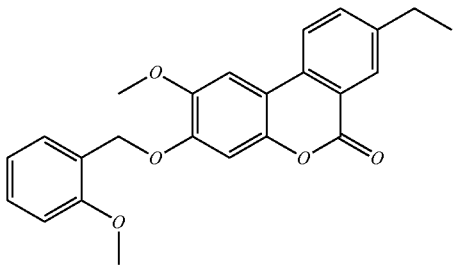
SG00559
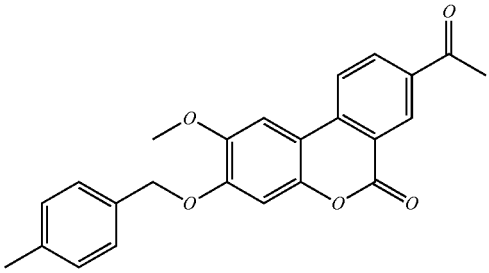
SG00560
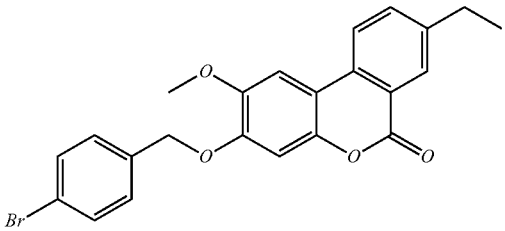

*-continued*

SG00568

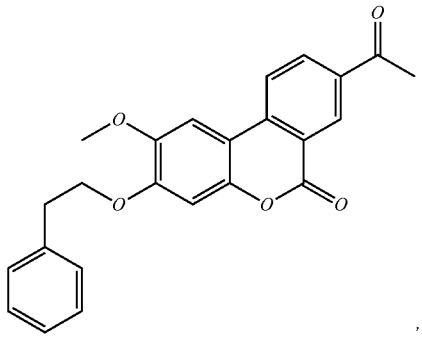

,

SG00573

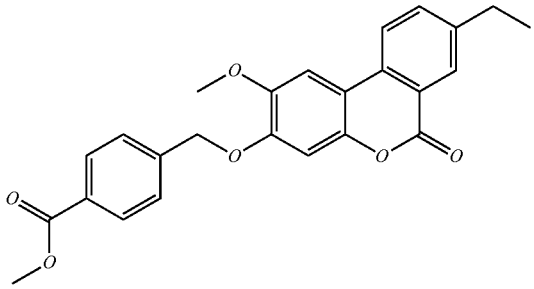

,

SG00574

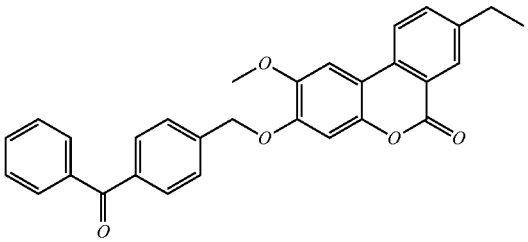

, *and*

SG00575

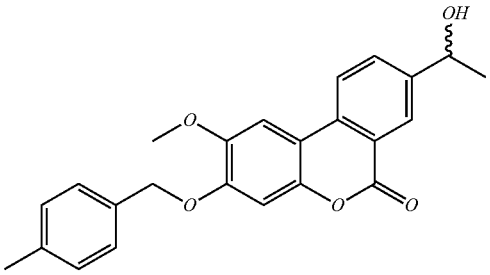

.

[2. The composition of claim 1, wherein said compound comprises

SG00629

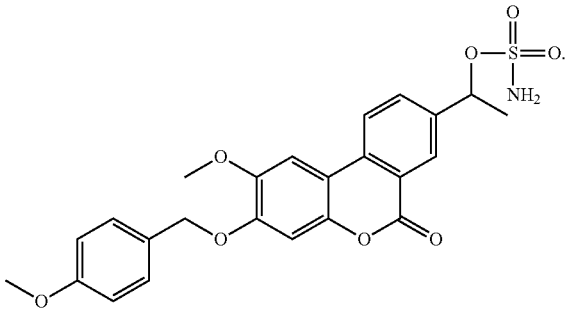

]

3. The composition of claim 1, wherein said composition is formulated in a biodegradable or non-biodegradable format for sustained release.

4. A method of treating cancer comprising administering an effective amount to a subject a composition of claim 1, wherein said cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, hemangioma, medullary carcinoma, bronchogenic carcinoma, renal cell carcinoma, hepatoma, bile duct carcinoma, choriocarcinomas, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, osteosarcoma, meningioma, melanoma, neuroblastoma, retinoblastoma, [acousticneuroma,] neurofibromas, trachoma and pyogenic granulomas, acute lymphocytic leukemia and acute myelocytic leukemia, chronic leukemia, polycythemia vera, lymphoma, multiple myeloma, Waldenstrom's [macroblobulinemia] *macroglobulinemia*, and heavy chain disease.

5. The method of claim 4 further comprising the co-administration to said subject said one or more compositions of Formula I and a therapeutic agent directed toward the treatment of said disease.

6. The method of claim 5, wherein said therapeutic agent is selected from the group consisting of an oncolytic agent, an anti-cancer agent, an anti-nausea agent and an anti-emesis agent.

7. The method of claim 4, wherein said administration includes topical, oral, nasal, rectal, and parenteral administration of said one or more compositions.

8. The method of claim 4, wherein said one or more compositions is coated on an implant.

9. The method of claim 8, wherein said device is a vascular stent.

*10. The composition of claim 1, wherein said compound according to Formula I is:*

SG00393

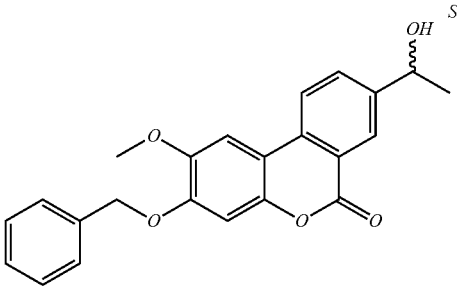

*11. The composition of claim 1, wherein said compound according to Formula I is:*

SG00527

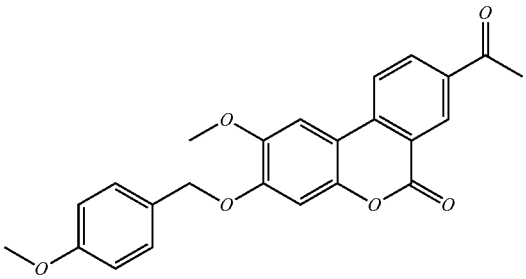

*12. The composition of claim 1, wherein said compound according to Formula I is:*

SG00528

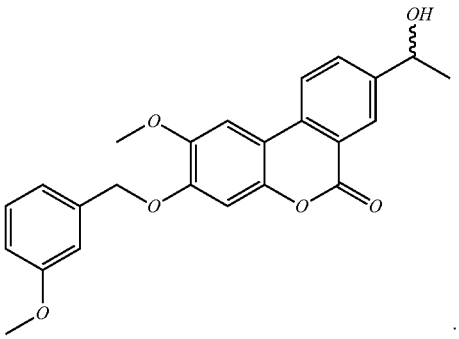

*13. The composition of claim 1, wherein said compound according to Formula I is:*

SG00529

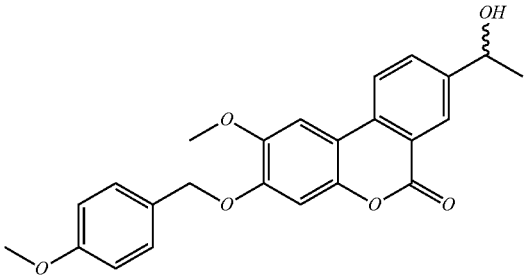

*14. The composition of claim 1, wherein said compound according to Formula I is:*

SG00545

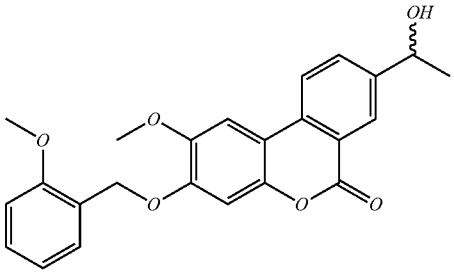

*15. The composition of claim 1, wherein said compound according to Formula I is:*

SG00546

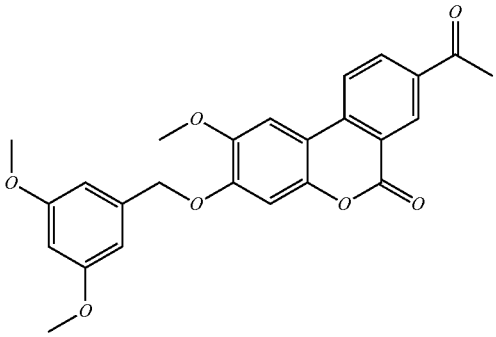

16. The composition of claim 1, wherein said compound according to Formula I is:

SG00547

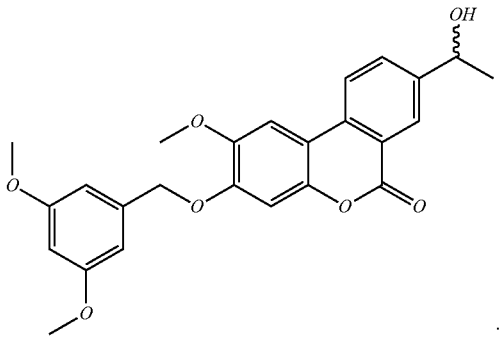

17. The composition of claim 1, wherein said compound according to Formula I is:

SG00550

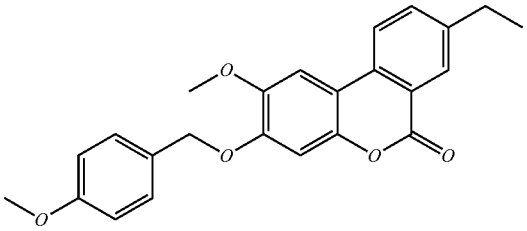

18. The composition of claim 1, wherein said compound according to Formula I is:

SG00551

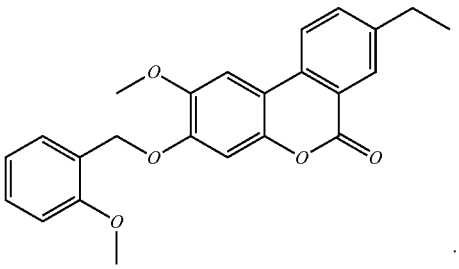

19. The composition of claim 1, wherein said compound according to Formula I is:

SG00559

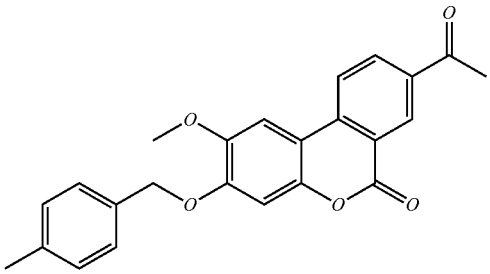

20. The composition of claim 1, wherein said compound according to Formula I is:

SG00560

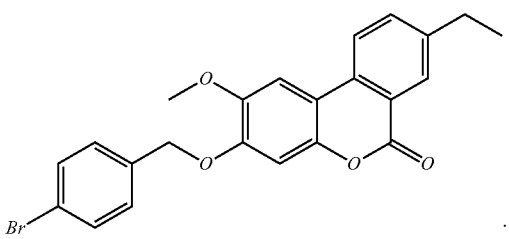

21. The composition of claim 1, wherein said compound according to Formula I is:

SG00568

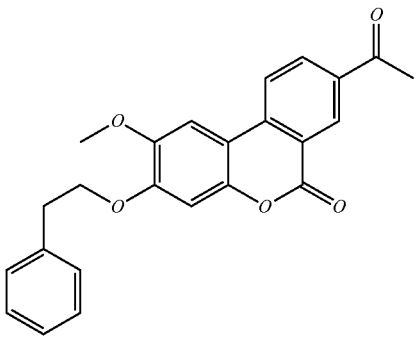

*22. The composition of claim 1, wherein said compound according to Formula I is:*

SG00573

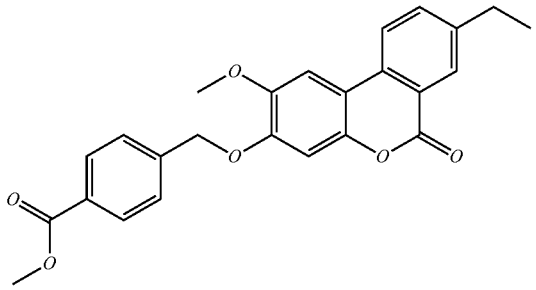

*23. The composition of claim 1, wherein said compound according to Formula I is:*

SG00574

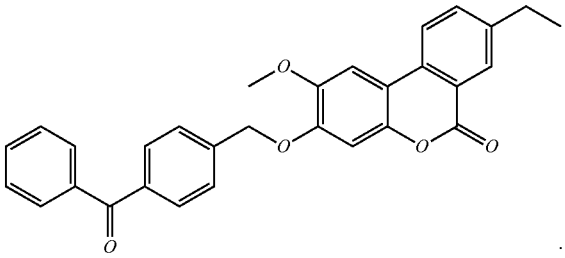

*24. The composition of claim 1, wherein said compound according to Formula I is:*

SG00575

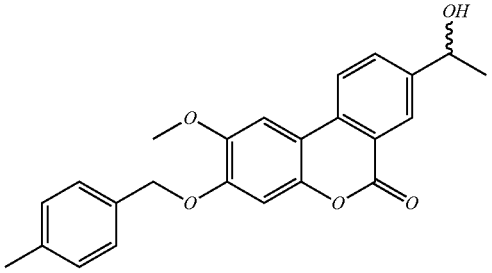

*25. The composition of claim 1, wherein said composition is a pharmaceutical composition further comprising a pharmaceutically acceptable carrier, diluent, or excipient.*

*26. The composition of claim 10, wherein said composition is a pharmaceutical composition further comprising a pharmaceutically acceptable carrier, diluent, or excipient.*

*27. The composition of claim 13, wherein said composition is a pharmaceutical composition further comprising a pharmaceutically acceptable carrier, diluent, or excipient.*

*28. The composition of claim 16, wherein said composition is a pharmaceutical composition further comprising a pharmaceutically acceptable carrier, diluent, or excipient.*

*29. The composition of claim 23, wherein said composition is a pharmaceutical composition further comprising a pharmaceutically acceptable carrier, diluent, or excipient.*

*30. The composition of claim 24, wherein said composition is a pharmaceutical composition further comprising a pharmaceutically acceptable carrier, diluent, or excipient.*

* * * * *